United States Patent [19]

Marcus et al.

[11] Patent Number: 5,231,472
[45] Date of Patent: Jul. 27, 1993

[54] COLOR MATCHING AND CHARACTERIZATION OF SURFACE COATINGS

[75] Inventors: Robert T. Marcus, Allison Park; Percy E. Pierce, Monroeville, both of Pa.

[73] Assignee: PPG Industries, Inc., Pittsburgh, Pa.

[21] Appl. No.: 760,651

[22] Filed: Sep. 16, 1991

[51] Int. Cl.$^5$ .................. G01D 3/50; G01N 21/27; G06F 15/46

[52] U.S. Cl. .................. 356/402; 356/405; 364/526

[58] Field of Search ................ 356/402, 405; 364/526

[56] References Cited

U.S. PATENT DOCUMENTS

| | | | |
|---|---|---|---|
| 3,389,265 | 6/1968 | Schreckendgust | 250/226 |
| 3,690,771 | 9/1972 | Armstrong, Jr. et al. | 250/226 |
| 3,885,878 | 5/1975 | Ishak | 250/226 |
| 3,916,168 | 10/1975 | McCarty et al. | |
| 3,999,864 | 12/1976 | Mutter | 356/418 |
| 4,449,821 | 5/1984 | Lee | 356/319 |
| 4,479,718 | 10/1984 | Alman | 356/405 |
| 4,572,672 | 2/1986 | Orchard eet al. | 356/446 |
| 4,583,858 | 4/1986 | Lebling et al. | 356/402 |
| 4,669,880 | 6/1987 | Nelson | 356/326 |
| 4,711,580 | 12/1987 | Venable | 356/328 |
| 4,917,495 | 4/1990 | Steenhoek | 356/328 |

OTHER PUBLICATIONS

Journal of the Optical Society of America, vol. 64, No. 7, pp. 991-992. "Basic Equations Used in Computer Color Matching", by Eugene Allen, Jul. 1974.
Progress in Organic Coatings, vol. 13, pp. 153-169 (1985), "Practical Pigment Testing with the Aid of the Kubelka-Munk Theory", Hans G. Volz.
Journal of the Optical Society of America, vol. 38, No. 5, "New Contributions to the Optics of Intensely Light--Scattering Materials, Part I" by P. Kubelka, May 1948, pp. 448-457.
Journal of the Optical Society of America, vol. 56, No. 9, Sep. 1966, pp. 1256-1259, entitled "Basic Equations Used in Computer Color Matching", by Eugene Allen.
Paint and Varnish Production, Aug. 1971, pp. 37-44, entitled "Computer Time-Sharing Aids Color Matching", by Dr. Ludwig Gall.
Progress in Organic Coatings, vol. 15, pp. 99-124, entitled "The Principle of Spectral Evaluation in Pigment Testing. A Review of 20 Year's Application of a Successful Method", (1987) by Hans G. Volz.
Journal of the Optical Society of America, vol. 32, pp. 727-736, entitled "Calculation of the Color of Pigmented Plastics", J. L. Saunderson. Dec. 1942.
Color Research and Application, published by John Wiley & Sons, Inc. (1977) vol. 2, No. 1, pp. 26-31, entitled "The Missing Variable: Internal Surface Reflection", by S. E. Orchard.

(List continued on next page.)

Primary Examiner—Vincent P. McGrawl
Attorney, Agent, or Firm—Linda Pingitore

[57] ABSTRACT

A method of characterization of a coating on a surface such as a paint coating having metallic flakes distributed within such coating. Single and multi-angle models are utilized. The coating is characterized by measurements having components of light reflected by the metal flakes and attenuated on its exit route from the coating, of light scattered in the entering path of the beam as it travels through the coating, of light scattered by the reflected beam on its exit from the coating, of light scattered in the entering path then reflected by the metallic flakes and attenuated in the coating on exiting, and of light scattering in the exit path, both to the metallic flake and reflected by the flake and attenuated on its exit from the coating. Methods of color matching a coating having a metallic flake distribution within the coating are included using reflectance factors and tristimulus values and minimizing the sum of the squares of the deviation between samples.

23 Claims, 3 Drawing Sheets

OTHER PUBLICATIONS

Ph.D Thesis, Rensselaer Polytechnic Institute, Troy, N.Y., Aug. 1972, entitled "Application of Turbid Medium Theory to Metallic Paint Systems", by Ellen de Dreux Campbell, (pp. i-3, 51-58, 64-84, 145-147).

Optica Acta, vol. No. 2, No. 4, pp. 153-162, Dec. 1955, entitled "Reflection by semi-infinite diffusers", by R. G. Giovanelli.

Journal of the Optical Society of America, vol. 59, No. 12, pp. 1584-1597, entitled "Reflection and Transmission of Light by Diffusing Suspensions", by S. E. Orchard. Dec. 1969.

A Treatise on Radiative Transfer, by V. V. Sobolev, published by D. Van Nostrand Company, Princeton, New Jersey, 1963, pp. 190-192.

Numerical Recipes, The Art of Scientific Computing, by William H. Press, Brian P. Flannery, Saul A. Teukolsky, and William T. Vetterling, Cambridge University Press, Cambridge, New York, 1986, pp. 274-277, 289-293.

"The Color and Appearance of Metallized Paint Films", Ph.D. Thesis Rensselaer Polytechnic Institute, Troy, New York, Nov., 1970, by J. G. Davidson.

"Radiative Transfer", by S. Chandrasekhar, originally published 1950 by Oxford University Press, republished by Dover Publications, New York, New York, 1960.

"Multiple Light Scattering—Tables, Formulas, and Applications", by H. C. van de Hulst, published by Academic Press, New York, New York, 1980.

COLOR MATCHING AND CHARACTERIZATION OF SURFACE COATINGS

BACKGROUND OF THE INVENTION

The Kubelka-Munk Mode

A two flux Kubelka-Munk model is widely used in the coatings industry for the color matching and batch correction of solid color coatings. This theory in its two constant version gives good color matches and batch corrections for solid color coatings in the pastel and midtone ranges. With dark colors the results are poorer but still usable. Coatings containing metallic flake have found wide acceptance in the automotive industry and are finding growing acceptance in the extrusion and industrial areas. These coatings exhibit a strong variation in appearance as the angle of view and illumination are changed. Attempts to color match coatings containing metal flakes using conventional color spectrophotometers and solid color matching software have been very disappointing. As a result, these coatings are often matched and batches corrected by visual tinting procedures.

Despite many efforts to extend the two flux Kubelka-Munk theory to metallic coatings, the poor agreement between predicted reflectance values, coating composition, and visual appearance has been disappointing. Part of the difficulty lies in the limitations of conventional 45/0 and diffuse/near-normal measuring geometry spectrophotometers to adequately characterize the appearance of coatings containing metallic flake. In addition, part of the poor agreement seems to be associated with the nature of the color matching algorithm itself.

The Kubelka-Munk model for a solid color considers a pigmented film of thickness $x_0$. Light falls on the film from above. The two flux Kubelka-Munk model considers a downward flux of light, I, and an upward flux, J. The downward flux is reduced by absorption and scattering and increased by the light scattered from the upward flux into the downward directed flux according to the equation $$-\frac{dI}{dx} = -(k+s)^*I + s^*J$$

where k is the absorption coefficient and s is the scattering coefficient of the film. The minus sign in the derivative is the result of taking the downward direction along the negative x axis.

The upward flux is reduced by absorption and scattering and increased by the light scattered from the downward flux into the upward directed flux according to the equation $$\frac{dJ}{dx} = -(k+s)^*J + s^*I$$

The film reflectance is defined as the ratio of the upward to the downward directed flux.

$$R = J/I$$

The rate of change of the reflectance with film thickness is obtained by differentiating the reflectance equation with respect to x.

$$\frac{dR}{dx} = (1/I)^* \frac{dJ}{dx} - (R/I)^* \frac{dI}{dx}$$

Substituting the expressions for dJ/dx, dI/dx, and making use of the definition of R, we obtain $$\frac{dR}{dx} = s - 2^*(k+s)^*R + s^*R^2$$

The reflectance R can be obtained by solving the differential equation for R. Alternatively the two simultaneous differential equations for I and J can be solved and R follows from the ratio of the upward to the downward flux. The complete solution is required for optically thin films and is of interest for hiding power and transparency calculations. At complete film hiding (infinite optical thickness) the solution simplifies to the form used for color matching and batch correction as used in commercial color matching software.

The solution of the differential equations for the fluxes I and J and the calculation of R for the Kubelka-Munk model are given in P. Kubelka, "New Contributions to the Optics of Intensely Light-Scattering Materials, Part I," Journal of Optical Society of America, 38, 448-457, 1948, along with a number of other useful relations. The final result for the reflectance of a film of thickness X over a substrate of reflectance $R_G$ is $$R = \frac{1 - R_G^*\{a - b^*\text{Coth}(b^*s^*X)\}}{a - R_G + b^*\text{Coth}(b^*s^*X)}$$

where
$a = 1 + k/s$;
$b = (a^2 - 1)^{\frac{1}{2}}$;
k is the absorption coefficient of the film;
s is the scattering coefficient of the film;
Coth($b^*s^*X$) is the hyperbolic cotangent of $b^*s^*X$.
Taking the limit of R as X tends to $\infty$ gives $$R_\infty = a - b$$

It is shown in the prior cited Kubelka article that $$a = \frac{1}{2}^*(1/R_\infty + R_\infty)$$

$$b = \frac{1}{2}^*(1/R_\infty - R_\infty)$$

The Kubelka-Munk equation relating to k/s to $R_\infty$ can easily be derived from $$k/s = a - 1$$

giving
$$k/s = (1 - R_\infty)^2/(2^*R_\infty)$$

This last relationship provides the basis for relating sample composition to $R_\infty$ (the film reflectance at complete hiding or an infinite optical film thickness) and is used in many applications of the Kubelka-Munk theory to industrial color matching. This equation is well known in the coatings and plastics industries and is used as the basis for color matching, batch correction and strength calculations.

An important, additional assumption in the theory is the additive character of k and s in relation to a film's composition. For a film containing N colorants, it is assumed that $$k = \sum_i^N k_i * c_i$$

$$s = \sum_i^N s_i * c_i$$

where $k_i$ is the absorption coefficient, $s_i$ is the scattering coefficient, and $c_i$ is the concentration of the ith colorant in the film. The summation is taken over the N colorants in the film.

If a film's composition is known along with the absorption and scattering coefficients of each colorant, then the k and s for that film can be calculated. The reflectance of the film then follows from the relationship $$R_\infty = 1 + (k/s) - \{(k/s)^2 + 2*(k/s)\}^{\frac{1}{2}}$$

which is the inverse of the equation previously given relating k/s to $R_\infty$.

Metallic Modifications to the Kubelka-Munk Model

Various attempts have been made to use the Kubelka-Munk model to color match metallic flake containing coatings. The earliest attempts involved preparing mixtures of aluminum flake and colored pigments and calibrating the aluminum flake pigment as if it were a white pigment. The predicted color matches and batch corrections using this procedure have been so unreliable that these operations are now routinely carried out by visual matching and tinting procedures.

J. G. Davidson (in a Ph.D. thesis, Rensselaer Polytechnic Institute in Troy, N.Y., February, 1971) proposed an alternate treatment of the metallic problem. He considered each aluminum flake as a single reflector with reflectance, r, and reflection cross section, $\sigma$. He proposed that the changes to the downward and upward fluxes are given by the equations $$-\frac{dI}{dx} = -(k + s + \sigma)*I + (s + r*\sigma)*J$$

$$-\frac{dJ}{dx} = -(k + s + \sigma)*J + (s + r*\sigma)*I$$

These equations differ from the previous Kubelka-Munk equations in that the aluminum flake pigment is assumed to remove light from the directed flux in proportion to its cross section, $\sigma$, and add light to the complimentary flux in amount $r*\sigma$ times the directed flux. The other pigments are assumed to contribute to the fluxes in the same manner as the preceding model for solid colors.

Substituting these equations into the equation for dR/dx we obtain $$\frac{dR}{dx} = (s + r*\sigma) = 2*(k + s + \sigma)*R + (s + r*\sigma)*R^2$$

This differential equation can be solved for R. The solution is identical to the above Kubelka-Munk solution if s is replaced by $(s+R*\sigma)$ and $(k+s)$ is replaced by $(k+s+\sigma)$.

The solution for a complete hiding layer can be derived directly from the condition dR/dx=0. This yields the result $$\frac{k + \sigma*(1 - r)}{s + r*\sigma} = \frac{(1 - R_\infty)^2}{2*R_\infty}$$

E. D. Campbell (in a Ph.D. thesis, Rensselaer Polytechnic Institute, Troy, N.Y., August, 1972) applied the Davidson modification to mixtures of metallic flake and colored pigments. Predictions for matching and batch corrections were shown to be unreliable.

Radiative Transfer Theory

S. Chandrasekhar in "Radiative Transfer Theory" (Oxford, Clarenden Press, 1950) describes the foundations of radiative transfer theory and applies this theory to a variety of astrophysical problems concerning steller atmospheres and planetary atmospheres. Of particular interest are the exposition of the foundations of radiative transfer theory and its application of this theory to the planetary atmosphere problem.

Chandrasekhar has investigated the angular scattering of planetary and stellar atmospheres and formulated the equations and methods to solve angular scattering problems. The basic equation of transfer for the angular intensity as a function of angle and optical depth is $$\mu \frac{dI(\tau,\mu,\phi)}{d\tau} = I(\tau,\mu,\phi) - \frac{1}{4\pi} \int_{-1}^{1} \int_{0}^{2\pi} p(\mu,\phi;\mu',\phi')I(\tau,\mu',\phi')d\mu'd\phi'$$

where

I is the intensity of the light incident on the coating;
$\tau$ is the optical depth of the coating;
$\mu$ is the cosine of the observation angle, $\theta_2$;
$\phi$ is the azimuthal angle of the observation;
$\mu'$ is the cosine of an illumination angle, $\theta'$;
$\phi'$ is an azimuthal angle; and
p is the scattering phase function.

Let the flux incident on surface of the coating be designated by F, the cosine of the angle of illumination by $\mu_o$, and the azimuthal angle of illumination by $\phi_o$.

It is sometimes convenient to distinguish between the reduced incident radiation $$\pi F e^{-\tau/\mu_o}$$

which penetrates to the level $\tau$ and the diffuse radiation field that arises from one or more scattering or reflection processes. The equation of transfer for the diffuse radiation field is $$\mu \frac{dI(\tau,\mu,\phi)}{d\tau} = I(\tau,\mu,\phi) - \frac{1}{4\pi} \int_{-1}^{1} \int_{0}^{2\pi} p(\mu,\phi;\mu',\phi')I(\tau,\mu',\phi')d\mu'd\phi' - \frac{1}{4} Fp(\mu,\phi; -\mu_o,\phi_o)e^{-\tau/\mu_o}$$

For a diffuse isotropic radiation field with an albedo $\Omega_o$, the equation of transfer is $$\mu \frac{dI(\tau,\mu)}{d\tau} = I(\tau,\mu) - \frac{\omega_o}{2} \int_{-1}^{1} I(\tau,\mu')d\mu' - \frac{1}{4} \omega_o F e^{-\tau/\mu_o}$$

This equation has been solved by Chandrasekhar who showed that the exact solution is $$I(0,\mu,\mu_o) = \frac{1}{4} \omega_o F \frac{\mu_o}{\mu + \mu_o} H(\mu)H(\mu_o)$$

where the $H(\mu)$ functions are defined by the nonlinear integral equation $$H(\mu) = 1 + \frac{1}{2} \omega_o \mu H(\mu) \int_0^1 \frac{H(\mu_o)}{\mu + \mu_o} d\mu_o$$

and can be numerically estimated by an iteration procedure described by Chandrasekhar. These functions have been tabulated by several investigators and can be computer generated on a personal computer.

Approximate Methods Based on Averaging Intensities

Prior to and since Chandrasekhar's exact solution to the problem many efforts have been made to solve the radiative transfer equation by approximate methods for various isotropic and anisotropic scattering models of interest in atmospheric science and technology.

One such method for isotropic scatterers was proposed by Schuster in "Radiation Through Foggy Atmospheres," Astrophys. Journal, 21, 1, 1905. This method involves the directional averaging of intensities.

Starting from the basic equation of transfer for isotropic scatterers $$\mu \frac{dI(\tau,\mu)}{d\tau} = I(\tau,\mu) - \frac{\omega_o}{2} \int_{-1}^1 I(\tau,\mu')d\mu'$$

where the reduced incident radiation is included with the scattered radiation, we define two average fluxes by the equations $$J = \int_0^1 I(\tau,\mu')d\mu'$$

and $$I = \int_{-1}^0 I(\tau,\mu')d\mu'$$

The flux J is an upward directed flux and the flux I is a downward directed flux.

Integrating the equation of transfer over $\mu$ from 0 to 1 and then over $\mu$ from 0 to $-1$ we obtain the following two equations $$\int_0^1 \mu \frac{dI(\tau,\mu)}{d\tau} d\mu = J - \frac{\omega_o}{2} (J + I)$$

$$\int_{-1}^0 \mu \frac{dI(\tau,\mu)}{d\tau} d\mu = I - \frac{\omega_o}{2} (J + I)$$

The integrals on the left sides of these equations can be approximated as follows.

$$\int_0^1 \mu \frac{dI(\tau,\mu)}{d\tau} d\mu \cong \int_0^1 \mu' d\mu' \frac{d}{d\tau} \int_0^1 I(\tau,\mu) d\mu = \frac{1}{2} \frac{dJ}{d\tau}$$

$$\int_{-1}^0 \mu \frac{dI(\tau,\mu)}{d\tau} d\mu \cong$$

$$\int_{-1}^0 \mu' d\mu' \frac{d}{d\tau} \int_{-1}^0 I(\tau,\mu) d\mu = -\frac{1}{2} \frac{dJ}{d\tau}$$

Combining these results, a set of simultaneous linear differential equations is obtained for the upward and downward fluxes.

$$\frac{1}{2} \frac{dJ}{d\tau} = J - \frac{\omega_o}{2} (J + I)$$

$$\frac{1}{2} \frac{dI}{d\tau} = -I + \frac{\omega_o}{2} (J + I)$$

Equations of this type have been used by many investigators to solve a variety of technical problems involving turbid materials. Kubelka and Munk in "Ein Beitrag zur Optik der Farbanstriche" (Z. Tech. Phys., 12, 593–601, 1931) derived similar equations which Kubelka ("New Contributions to the Optics of Intensely Light-Scattering Materials, Part I," Journal Opt. Society of Am., 38, 448–457, 1948) cast into the form that is widely used today for color matching coatings, plastics, inks, and related materials.

A Radiative Transfer Derivation of the Kubelka-Munk Equation

Kubelka and Munk derived their turbid media theory without consideration of the more rigorous radiative transfer equation. The following line of thought establishes the relation between the average flux equations derived from the radiative transfer equation and the Kubelka-Munk equations.

The albedo of the material, $\omega_o$, is related to the absorption coefficient, K, and a scattering coefficient, S, of the material by the relation $$\omega_o = S/(K+S)$$

The optical depth $\tau$ is related to K, S, and the distance x inside the material by the relation $$\tau = (K+S) x$$

Introducing these relationships and rearranging the differential equations for the averaged intensities result in the Kubelka-Munk equations $$\frac{dJ}{dx} = -(k + s)^* J + s^* I$$

$$\frac{dI}{dx} = (k + s)^* I - s^* J$$

In these equations x is the distance from the unilluminated surface according to Kubelka-Munk rather than the distance from the illuminated surface which is the convention used for the radiative transfer equations. The Kubelka-Munk absorption coefficient, k, and scattering coefficient, s, are related to the radiative transfer absorption coefficient, K, and scattering coefficient, S, by $$s = S/2$$

$k = 2K$

These equations are strictly valid for diffuse illumination and diffuse viewing conditions. These conditions are seldom encountered in practice. Despite this limitation the results obtained using 45/0 and diffuse near normal instruments has been very satisfactory for pastel and midtone solid color materials. The results for deeptone or dark materials have been less satisfactory but usable for industrial color matching.

In the case of materials showing strong directional appearance characteristics such as metal flake pigmented coatings, pearlescent pigmented coatings, etc., the theory has been inadequate to such an extent that these materials are matched by visual matching methods.

The inability of average flux approximations to predict the angular variation of coating appearance is the main reason for the failure efforts to modify the Kubelka-Munk equations to handle metal flake containing coatings. These and other efforts have treated the metal flakes as another pigment perhaps with anisotropic scattering characteristics along with the color pigments. The color pigments are typically a fraction of a wavelength of the incident light in size while the metal flakes range in size from 60 to 200 times the wavelength of light. Further the metal flakes are opaque to and are moderate to good reflectors of incident light.

An Approximate Radiative Transfer Solution for Isotropic Scattering

Approximate solutions to the radiative transfer equations based upon averaging fluxes lead to useful formulas for determining the constants for the colored pigments used in metallic coatings and for color matching solid colors.

The diffuse radiative transfer equation for isotropic scatterers having an albedo of $\omega_o$ is $$\mu \frac{dI(\tau,\mu)}{d\tau} = I(\tau,\mu) - \frac{\omega_o}{2} \int_{-1}^{1} I(\tau,\mu')d\mu' - \frac{1}{4} \omega_o F e^{-\tau/\mu_o}$$

which can be rewritten as $$\mu \frac{dI(\tau,\mu)}{d\tau} = I(\tau,\mu) - S(\tau)$$

where $$S(\tau) = \frac{\omega_o}{2} \int_{-1}^{1} I(\tau,\mu')d\mu' + \frac{1}{4} \omega_o F e^{-\tau/\mu_o}$$

The intensity of scattered light in the direction $\mu$ to an observer outside the coating film for incident collimated light coming from a direction $\mu_o$ is $$I(0,\mu,\mu_o) = \frac{1}{\mu} \int_0^{\infty} S(\tau) e^{-\tau/\mu} d\tau$$

If we can obtain an approximate expression for $S(\tau)$, we can perform the integration over $\tau$ and calculate the reflected light intensity for the coating film. We assume here a film of infinite optical thickness which corresponds to the important case of a completely hiding coating layer.

The approximate diffuse flux equations for isotropic scatterers can be solved to give estimates of the upward and downward diffuse fluxes.

$$\frac{1}{2} \frac{dJ}{d\tau} = J - \frac{\omega_o}{2} (J + I) - \frac{1}{4} \omega_o F e^{-\tau/\mu_o}$$

$$\frac{1}{2} \frac{dI}{d\tau} = -I + \frac{\omega_o}{2} (J + I) + \frac{1}{4} \omega_o F e^{-\tau/\mu_o}$$

These equations are for the diffuse fluxes since we have separated out the direct intensity from the diffuse intensity in the radiative transfer equation given above. Solution of these equations for I and J gives $$J = \frac{\omega_o F \mu_o}{2(1 - \lambda\mu_o)(1 + \lambda\mu_o)} \left[ (1 + 2\mu_o) \frac{(1 - \lambda/2)}{(1 + \lambda/2)} e^{-\lambda\tau} + (1 - 2\mu_o) e^{-\tau/\mu_o} \right]$$

$$I = \frac{\omega_o F \mu_o}{2(1 - \lambda\mu)(1 + \lambda\mu)} [(1 + 2\mu_o) e^{-\lambda\tau} - (1 + 2\mu_o) e^{-\tau/\mu_o}]$$

where $$\lambda = 2(1 - \omega_o)^{\frac{1}{2}}$$

The source function $S(\tau)$ then is estimated by $$S(\tau) = \frac{\omega_o}{2} (J + I) + \frac{1}{4} \omega_o F e^{-\tau/\mu_o}$$

$$S(\tau) = \frac{\omega_o^2 F \mu_o}{2(1 - \lambda\mu_o)(1 + \lambda\mu_o)} \left[ \frac{(1 + 2\mu_o)}{(1 + \lambda/2)} e^{-\lambda\tau} - 2\mu_o e^{-\tau/\mu_o} \right] + \frac{1}{4} \omega_o F e^{-\tau/\mu_o}$$

Introducing this result into the equation for $I(0,\mu,\mu_o)$ and performing the integration over $\tau$, we obtain after some algebra $$I(0,\mu,\mu_o) = \frac{1}{4} \omega_o F \frac{\mu_o}{\mu + \mu_o} \left[ \frac{1 + 2\mu}{1 + \lambda\mu} \right] \left[ \frac{1 + 2\mu_o}{1 + \lambda\mu_o} \right]$$

This equation can be related to the exact result obtained by Chandrasekhar, if we set the $H(\mu)$ function equal to $$H(\mu) = \frac{1 + 2\mu}{1 + \lambda\mu}$$

This simple relation is a good estimate for the $H(\mu)$ functions and also gives a good estimate of the exact value of the radiance factor, $\beta(\mu,\mu_o)$.

$$\beta(\mu,\mu_o) = \frac{1}{4} \frac{\omega_o}{\mu + \mu_o} H(\mu)H(\mu_o)$$

It can be used as a starting point to calculate the exact $H(\mu)$ functions and is useful for the estimation of calibration constants for colored pigments used in metallic coatings.

This equation is also sufficiently accurate for color matching calculations for solid colors.

Bridgeman in "Two-flux Formulae for the Total and Directional Reflectance of a Semi-infinite Diffuser" (Die Farbe, 35/36, 41–49, 1988/1989) has proposed similar approximations to the $H(\mu)$ functions and has arrived at the same formula for the $H(\mu)$ function given above by a process of empirical fitting his two flux solutions to exact computer generated $H(\mu)$ function data.

A useful insight into the physical significance of J and I, the upward and downward averaged fluxes, can be obtained by evaluating the upward flux for $\tau=0$ $$J(0) =$$

$$\frac{\omega_o F \mu_o}{2(1 - \lambda\mu_o)(1 + \lambda\mu_o)} \left[ (1 + 2\mu_o)\frac{(1 - \lambda/2)}{(1 + \lambda/2)} + (1 - 2\mu_o) \right]$$

After rearrangement J becomes $$J = F\mu_o \left[ 1 - \frac{(1 + 2\mu_o)}{(1 + \lambda\mu_o)} \frac{\lambda}{2} \right]$$

or $$J = F\mu_o [1 - H(\mu_o)(1 - \omega_o)^{\frac{1}{2}}]$$

This last expression is the well-known result for the total reflected flux from a surface illuminated by a collimated beam of light of intensity $\pi F$ from a direction $\mu_o$ (see R. G. Giovanelli, "Reflection by Semi-infinite Diffusers," Optical Acta, 2, 153–62, 1955).

Giovanelli shows that the radiance factor for diffuse illumination and viewing from a direction $\mu$ is given by $$\beta = 1 - H(\mu)(1 - \omega_o)^{\frac{1}{2}}$$

This important result applies to the diffuse/near normal type of measurement geometry in widespread use in commercial color measuring equipment.

SUMMARY OF THE INVENTION

Characterization of coatings, such as metallic paints, is made by representing the reflected and scattered light as having components from the following: light from the incident beam which is reflected by the metal flake towards the observer; light scattered by the colored pigments which is reflected by the metal flake towards the observer; and light scattered by the colored pigments towards the observer.

The radiance factor of a metal flake containing coating is given by the sum of the direct radiance contribution of the incident beam reflected by the metal flake and the scattered light contribution to the radiance $$\beta(\mu,\phi;\mu_o,\phi_o) = \frac{\sigma\mu\mu_o \beta^*(\mu,\phi;\mu_o,\phi_o)}{(\mu + \mu_o)(K + S) + \sigma\mu\mu_o} + \beta_s$$

in which $$\beta^*(\mu,\phi;\mu_o,\phi_o) = \frac{r(\mu,\phi;\mu_o,\phi_o)}{2\mu}$$

A good first approximation is to assume the metal flakes are perfect mirrors reflecting light with no loss or attenuation. The scattered light contribution to the radiance then becomes $$\beta_s =$$

$$\frac{S}{2}\left[ \frac{1}{2(\mu + \mu_o)(K + S) + \sigma\mu\mu_o} + \frac{\sigma}{(2(K + S) + \sigma\mu_o)(2(K + S) + \sigma\mu)} \right]$$

If the metal flakes are assumed to be specular ("mirror") reflectors that have some loss or attenuation, the scattered reflected light contribution is $$\beta_s = \frac{\omega_o}{4(\mu + \mu_o)} \left[ 1 + \frac{\{r(\mu_o) r(\mu) - 1\}\sigma\mu\mu_o}{(\mu + \mu_o)(K + S) + \sigma\mu\mu_o} - \right.$$

$$\left. \frac{r(\mu_o) r(\mu)\sigma\mu\mu_o}{2(\mu + \mu_o)(K + S) + \sigma\mu\mu_o} \right] +$$

$$\frac{\omega_o}{4(\mu - \mu_o)} \left[ \frac{r(\mu_o) \sigma\mu}{2(K + S) + \sigma\mu} + \right.$$

$$\left. \frac{\{r(\mu_o) - r(\mu)\}\sigma\mu\mu_o}{(\mu + \mu_o)(K + S) + \sigma\mu\mu_o} - \frac{r(\mu_o) \sigma\mu_o}{2(K + S) + \sigma\mu_o} \right]$$

This result differs from previous methods in that each metal flake is treated as a reflecting substrate rather than a pigment and then the total optical effect is found by integrating over the metal flake distribution in the film.

Color matching and batch correction can be made using the above characteristics by wavelength matching to the spectrophotometric reflectance curve simultaneously at each illuminating and viewing geometry of interest. A wavelength match may be refined by using tristimulus iteration procedures. The tristimulus procedure includes requiring that the sums of the squares of the deviations of the match tristimulus values from the standard for three illuminants to be a minimum at each geometry. This procedure has the advantage that it produces the least metameric match to the standard using the three X, Y, Z values for the primary illuminant, but requires highly repeatable and reproducible instrumental measurements.

DESCRIPTION OF PREFERRED EMBODIMENTS

Radiative Transfer Theory for Metallic Coatings

We model a colored metallic coating as a collection of metallic reflecting plates imbedded in a medium containing isotropic scattering colored pigments. The metal flakes are oriented more or less parallel to the film surface.

Figure 1:
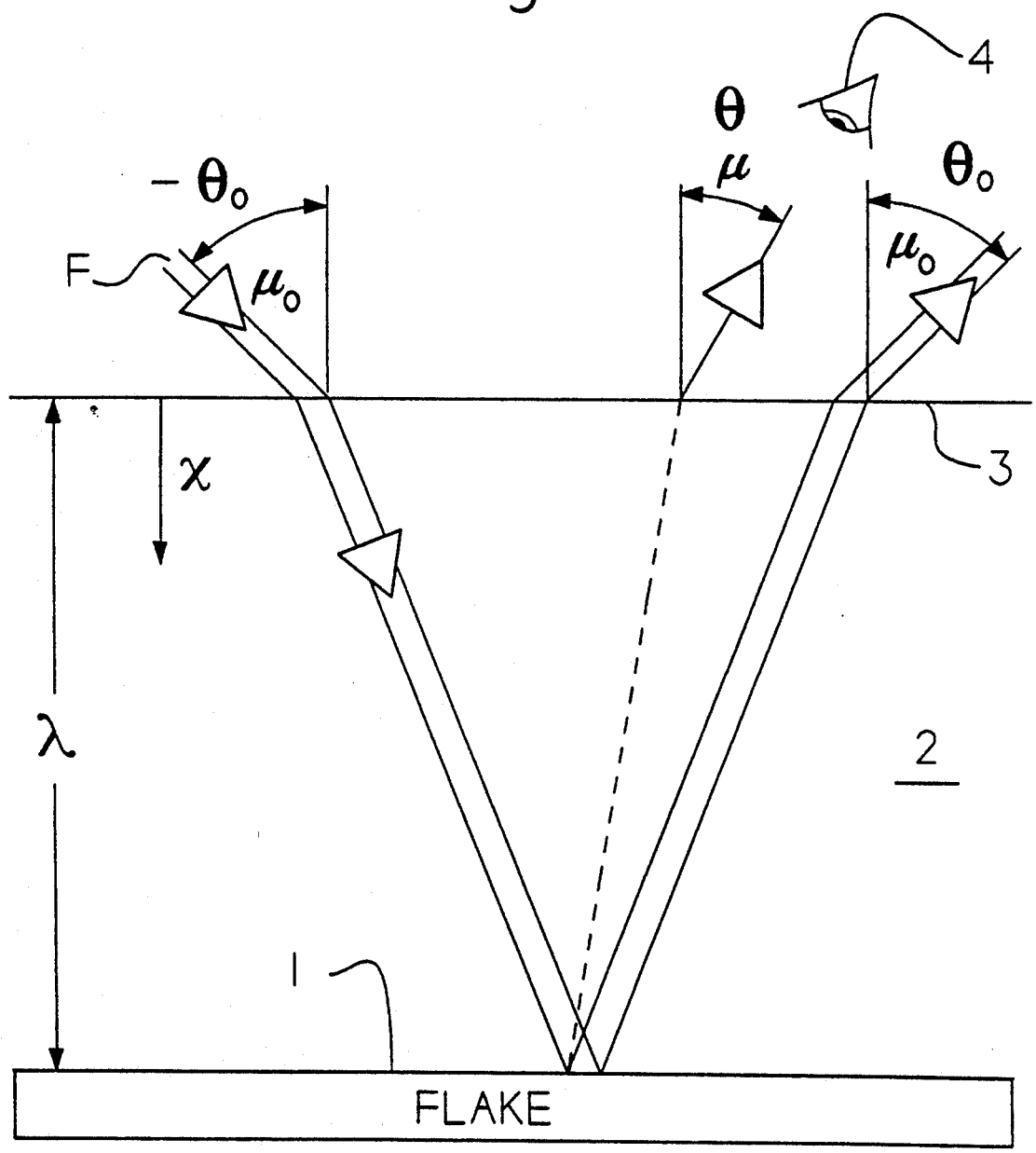
FIG. 1 is a diagrammatic representation of a metallic coating in cross-section showing an aluminum flake embedded a distance, $\tau$, in a pigmented film.

Consider a collimated beam, F, of light incident as shown in FIG. 1 at an angle $-\theta_o$ to the outwardly drawn normal on a metal flake containing coating, 2. The flake, 1, is embedded in a medium pigmented with absorbing and scattering colored pigments. The flake, 1, is oriented generally parallel to the surface 3 of the coating, 2, at an optical depth $\tau$ from the air/coating interface.

Neglecting for the present the refraction effects that occur at the air/coating boundary, the incident flux F enters the medium and is attenuated by absorption and scattering as it travels through the film.

The collimated attenuated beam will reach the metal flake and be reflected at various angles with reflection coefficient $r(\mu,\mu_o)$ where $\mu$ is the direction cosine of the angle of reflection $\theta$ and $\mu_o$ is the direction cosine of the angle of the incident beam $\theta_o$.

The intense incident beam will be specularly reflected at the specular angle $\theta_o$ with direction cosine $\mu_o$, pass through the film again, and be attenuated by absorption and scattering as it travels through the layer of optical thickness $\tau$ and leaves the film.

An observer viewing the film at an angle $\theta$ (direction cosine $\mu$) will see all the light scattered and reflected in the direction $\mu$. In all future references to direction the reference will be to the direction cosines since they play a fundamental role in radiative transfer calculations.

The scattered and reflected light in the direction $\mu$ seen by the observer will consist of the following components:

a. light from the incident beam reflected by the metal flake in the direction $\mu$ and attenuated as it leaves the film in the direction $\mu$.
b. light scattered by the primary beam in the direction $\mu$ as it travels through the layer of optical thickness $\tau$.
c. light scattered in the direction $\mu$ by the reflected primary beam as it leaves the film in the direction $\mu_o$ through the layer of optical thickness $\tau$.
d. light scattered in the layer $\tau$ by the incident beam in the direction of the flake, reflected by the flake in the direction $\mu$, and attenuated as it travels out of the film through the layer of thickness $\tau$ to the observer.
e. light back scattered by the exiting primary beam toward the metal flake in the direction $-\mu$, reflected by the flake in the direction $\mu$, and attenuated on its way to the observer in the layer of optical thickness $\tau$.

These contributions of scattered and reflected light seen by the observer 4 will be calculated and summed to give the intensity of light viewed by an observer from a direction $\mu$ for a single metal flake 1 embedded in a medium coating 2 containing absorbing and scattering colored pigments.

We shall first calculate the optical effect of a single aluminum flake imbedded in the film containing isotropic scattering color pigments and then sum this optical effect over the aluminum flake distribution to obtain the total intensity of scattered and reflected light for the coating.

To accomplish our calculation we will rely on results and methods used by astronomers who have studied the planetary atmosphere problem.

The coating film containing the colored pigments will correspond to the planetary atmosphere and the aluminum flake will represent the ground with arbitrary reflecting characteristics. The combined effect of the colored pigmented layer and flake is represented by R.

Using the operators and the adding or doubling method described by H. C. van de Hulst in Multiple Light Scattering, Tables, Formulas, and Applications, Volumes 1 and 2 (Academic Press, New York and London, 1980), we obtain the following result $$R = R_f + T_f R_a [1 + R_f R_a + (R_f R_a)^2 + \ldots] T_f$$

where
$R_f$ is the reflection function for the pigmented layer;
$T_f$ is the transmission function for the pigmented layer;
$R_a$ is the reflection function for the aluminum flake.

For an arbitrary flake reflection function no further simplification is possible and the expression for R must be evaluated term by term by successively applying these operator functions in the order indicated.

Once R is known, the reflected intensity, I, can be calculated from the incident intensity, $I_o$, from the relation $$I = R \, I_o$$

where the above operator equation involves the evaluation of the following integral.

$$I(\mu,\phi) = \frac{1}{\pi} \int_0^{2\pi} d\phi_o \int_0^1 R(\mu,\phi,\mu_o,\phi_o) I_o(\mu_o,\phi_o) \mu_o d\mu_o$$

A similar operator equation gives the transmitted light intensity, I, from the incident light intensity, $I_o$.

$$I = T \, I_o$$

$$I(\mu,\phi) = \frac{1}{\pi} \int_0^{2\pi} d\phi_o \int_0^1 T(\mu,\phi,\mu_o,\phi_o) I_o(\mu_o,\phi_o) \mu_o d\mu_o$$

The evaluation of expressions for R and T for various physical models and materials is the subject of many papers in astrophysics and meteorology according to van de Hulst.

Because the pigments used in metallic coating films are dispersed to a high degree of transparency in order to give the maximum appearance change with varying angles of view and illumination, the partially transparent atmosphere model is a good physical approximation to describe metallic coatings.

PARTIALLY TRANSPARENT ATMOSPHERE MODEL

Because single scattering and reflection events are physically most significant for a partially transparent atmosphere it is possible to obtain relatively simple mathematical expressions for the reflected and scattered light intensities.

Our development of the calculation of the various contributions to the reflected intensity will consist of two parts.

The major contribution to the reflected intensity comes from the attenuation of the primary incident beam as it travels through the pigmented layer, is reflected by the metal flake toward the observer, and is attenuated again by the pigmented layer before reaching the observer.

A smaller but significant contribution to the reflected intensity comes from the scattering of light by colored pigments and reflection of this scattered light by the metal flake in the direction of the observer.

These contributions will be calculated separately for a single metal flake imbedded in a film containing colored pigments, added together, and then summed over the metal flake distribution to obtain the total optical effect.

a. Direct Reflection by the Attenuated Incident Beam

Consider a single plate located inside the film at an optical depth $\tau$ from the surface that is illuminated by a collimated beam of light of intensity $\pi F$ from a direction $-\theta_o$ from the outwardly drawn normal to the surface.

As the incident beam travels through the film it will be attenuated by absorption and scattering. At the metal flake surface it will have the intensity $$\pi F \, e^{-\tau/\mu_o}$$

After reflection by the metal flake in the direction $(\mu,\phi)$ the intensity will be $$\tfrac{1}{4}\sigma_o F \, r(\mu,\phi;\mu_o,\phi_o)\mu_o e^{-\tau/\mu_o}$$

where $\sigma_o$ is the area of the metal flake which is the order of a 1000 to 10,000 times larger than the colored pigment particles.

The intensity contribution from a single metal flake viewed by an observer from the direction $\mu, \phi$ outside the film will be $$\tfrac{1}{4}\sigma_o F \, r(\mu,\phi;\mu_o,\phi_o)(\mu_o/\mu) e^{-\tau/\mu} e^{-\tau/\mu_o}$$

The total intensity viewed by the observer $(\mu,\phi)$ is the sum of the contributions from all the flakes in the film distributed at different optical depths.

Various metal flake distributions can be postulated. For a uniform distribution of metal flakes, the cumulative fractional film area covered by metal flakes, $P(\tau)$, can be shown to be $$P(\tau) = 1 - e^{-\tau/\tau_o}$$

where $\tau_o$ is an optical depth parameter that depends on $\sigma_o$, the area of a metal flake, $c$, the concentration of metal flakes per unit volume, and $(K+S)$ the optical constants of the colored pigments in the film according to the equation $$\tau_o = (K+S)/(\sigma_o c) = (K+S)/\sigma$$

The derivative of $P(\tau)$ with respect to $\tau$ gives the fraction of flake coverage in the layer $\tau, \tau+d\tau$.

$$dP(\tau)/d\tau = (1/\tau_o) e^{-\tau/\tau_o}$$

The total intensity of light viewed by the observer $(\tau,\phi)$ is equal to $$I(0,\mu,\phi;\mu_o,\phi_o) = F\mu_o \frac{r(\mu,\phi;\mu_o,\phi_o)}{2\mu\tau_o} \int_0^\infty e^{-\eta/\mu_o} e^{-\eta/\mu} e^{-\tau/\tau_o} d\eta$$

where the integral or summation of flake reflections is taken over the depth of the film which is considered here to be an infinite half plane or a completely covering optical layer.

Performing the integration and introducing the expression for $\tau_o$ $$I(0,\mu,\phi;\mu_o,\phi_o) = F\mu_o \frac{r(\mu,\phi;\mu_o,\phi_o)}{2\mu} \frac{\sigma\mu\mu_o}{(\mu+\mu_o)(K+S)+\sigma\mu\mu_o}$$

defining $$\beta(\mu,\phi;\mu_o,\phi_o) = I(0,\mu,\phi;\mu_o,\phi_o)/F\mu_o$$

and $$\beta^*(\mu,\phi;\mu_o,\phi_o) = \frac{r(\mu,\phi;\mu_o,\phi_o)}{2\mu}$$

we obtain the result $$\beta(\mu,\phi;\mu_o,\phi_o) = \frac{\sigma\mu\mu_o \, \beta^*(\mu,\phi;\mu_o,\phi_o)}{(\mu+\mu_o)(K+S)+\sigma\mu\mu_o}$$

which accounts for the optical properties of the metallic film except for the weak scattering of the transparent color pigments used to color the metal flake coating.

b. Scattered Light Reflections

The estimation of the weak scattering is a critical aspect of the theory since this weak scattering is responsible for the difference in flop between different coatings that have the same face appearance. The reflection and transmission functions for first order scattering in an optical layer of thickness $\tau$ are $$R(\mu,\mu_o) = \frac{\omega_o}{4(\mu+\mu_o)} [1 - e^{-\tau/\mu} e^{-\tau/\mu_o}]$$

and $$T(\mu,\mu_o) = \frac{\omega_o}{4(\mu-\mu_o)} [e^{-\tau/\mu} - e^{-\tau/\mu_o}]$$

Because of the strongly directional nature of the metal flake scattering, we can approximately model the flake particles in the correction term as being specular reflectors.

i. Ideal Specular Reflector

In the case of an ideal or perfect specular reflector, the incident and scattered light will be reflected at the flake surface like a mirror with no loss or attenuation. The net optical effect can be obtained by reflecting the layer into its mirror image. Following Van de Hulst, the reflection function for the scattered light will then consist of the sum of the reflection and transmission functions for a single layer of thickness $2\tau$.

$$R_s(\mu,\mu_o,\phi,\tau) = R(\mu,\mu_o,\phi,2\tau) + T(\mu,\mu_o,\phi,2\tau)$$

For collimated incident radiation $$I_o = \pi F \delta(\mu - \mu_o)\delta(\phi - \phi_o)$$

the intensity is given by $$I = R_s(\mu, \mu_o, \phi_o, \tau) I_o$$

which is equal to $$I = \frac{\omega_o \mu_o F}{4(\mu + \mu_o)} [1 - e^{-2\tau/\mu} e^{-2\tau/\mu_o}] + \frac{\omega_o \mu_o F}{4(\mu - \mu_o)} [e^{-2\tau/\mu} - e^{-2\tau/\mu_o}]$$

This result for the scattered light intensity for a single metal flake must be summed over all the metal flakes in the film and added to the contribution from the direct component to give the total intensity seen by an observer outside the film.

Integrating this result over the metal flake distribution we obtain $$\beta_s = \frac{S}{2} \left[ \frac{1}{2(\mu + \mu_o)(K + S) + \sigma\mu\mu_o} + \frac{\sigma}{(2(K+S) + \sigma\mu_o)(2(K+S) + \sigma\mu)} \right]$$

ii. Partial Specular Reflector

In the case of a specular reflector with a reflection function $$R_a = r(\mu)[\delta(\mu - \mu_o)/2\mu]2\pi \delta(\phi - \phi_o)$$

where $r(\mu)$ is the reflection coefficient of the flake for light incident from a direction $\mu$, a more involved calculation gives the following result for the scattered light reflected intensity $$I = \frac{\omega_o \mu_o F}{4(\mu + \mu_o)} [1 + \{r(\mu_o)r(\mu) - 1\} e^{-\tau/\mu} e^{-\tau/\mu_o} - r(\mu_o)r(\mu) e^{-2\tau/\mu} e^{-2\tau/\mu_o}] + \frac{\omega_o \mu_o F}{4(\mu - \mu_o)} [r(\mu) e^{-2\tau/\mu} + \{r(\mu_o) - r(\mu)\}e^{-\tau/\mu_o} e^{-\tau/\mu} - r(\mu_o)e^{-2\tau/\mu_o}]$$

This result reduces to our previous expression for a perfect specular reflector if both $r(\mu)$ and $r(\mu_o)$ are set equal to one.

Integrating these equations for a single metal flake over the assumed uniform aluminum flake distribution in the coating, we obtain the result $$\beta_s = \frac{\omega_o}{4(\mu + \mu_o)} \left[ 1 + \frac{\{r(\mu_o)r(\mu) - 1\}\sigma\mu\mu_o}{(\mu + \mu_o)(K + S) + \sigma\mu\mu_o} - \frac{r(\mu_o)r(\mu)\sigma\mu\mu_o}{2(\mu + \mu_o)(K + S) + \sigma\mu\mu_o} \right] + \frac{\omega_o}{4(\mu - \mu_o)} \left[ \frac{r(\mu)\sigma\mu}{2(K + S) + \sigma\mu} + \frac{\{r(\mu_o) - r(\mu)\}\sigma\mu\mu_o}{(\mu + \mu_o)(K + S) + \sigma\mu\mu_o} - \frac{r(\mu_o)\sigma\mu_o}{2(K + S) + \sigma\mu_o} \right]$$

This result reduces to the simpler perfect specular reflector result if both $r(\mu)$ and $r(\mu_o)$ are set equal to one.

c. Combined Direct and Scattered Reflected Light

The reflectance of a metal flake containing coating is given by the sum of the direct radiance contribution and the scattered light contribution to the radiance.

$$\beta(\mu,\phi;\mu_o,\phi_o) = \frac{\sigma\mu\mu_o\beta^*(\mu,\phi;\mu_o,\phi_o)}{(\mu + \mu_o)(K + S) + \sigma\mu\mu_o} + \beta_s$$

In the case of bright aluminum flake coatings, the perfect specular approximation gives very good estimates of the observed reflectance. For metal flakes with lower reflectances, the more complicated result for partial specular reflectors is required.

As in the Kubelka-Munk theory, it is assumed that the nonmetallic colorants in the film contribute additively to K and S. Thus $$K = \Sigma_i K_i^* c_i$$

$$S = \Sigma_i S_i^* c_i$$

where $K_i$ is the absorption coefficient, $S_i$ is the scattering coefficient, and $c_i$ is the concentration of the ith nonmetallic colorant. The summations are taken over the number of nonmetallic colorants in the film.

If more than one aluminum pigment is present in the film, then $\sigma$ is given by $$\sigma = \sum_i \sigma_i^* c_i$$

where $\sigma_i$ is the cross section of the ith aluminum pigment. The summation is taken over the number of aluminum pigments in the film.

FIRST SURFACE CORRECTIONS

The above reflectance is derived without regard for the external and internal reflections that take place at the air coating interface. Better color matching predictions may be obtained for coatings if a correction is made for these reflections. The rigorous radiative transfer equations for making surface corrections are formulated by V. V. Sobolev (in A Treatise on Radiative Transfer, D. Van Nostrand Company, Inc., Princeton, N.J., 1963), R. G. Giovanelli ("Reflection by Semi-infinite Diffusers," Optical Acta, Vol. 2, No. 4, December, 1955, pp. 153-162), and S. E. Orchard ("Reflection and Transmission of Light by Diffusing Suspensions," Journal Optical Soc. of Am., 59, 1584-1597). The approximations to the rigorous radiative transfer equations proposed by J. L. Saunderson in "Calculation of the Color of Pigmented Plastics," Journal Optical Soc. of Am., 32, 727-736, 1942, are the most widely used equations for diffuse/near-normal measurements.

The scattering and reflecting pigments in a metallic film are dispersed in a resin matrix while the film reflectance is measured in air. The refractive index of the resin matrix is generally about 1.5 while the refractive index of air is 1.

An incident collimated beam of light of flux $\pi F(m)$ per unit area falling on the coating film will be refracted at the plane parallel film surface as it crosses from a region of lower to a region of higher refractive index.

If m is the cosine of the external angle of incidence, then the cosine of the internal angle of incidence, $\mu_o$, is given by Snell's law of refraction $$1 - m^2 = n^2(1-\mu_o)^2$$

where n is the ratio of the refractive index of the resin matrix to that of air.

Assuming the upper surface of the coating film is a specular reflector, its directional reflection characteristics are described by Fresnel's equations.

The incident illumination is $\pi F(m)m$. The direct flux immediately below the film surface, measured on a plane parallel to the beam, is $$\pi F(m) \frac{m}{\mu_o} t(m)$$

where $$t(m) = 1 - r(m)$$

and $$r(m) = \frac{1}{2} \left[ \left( \frac{a-m}{a+m} \right)^2 + \left( \frac{n^2 m - a}{n^2 m + a} \right)^2 \right]$$

$$a^2 = n^2 - \sin^2\theta$$
$$n = n_2/n_1$$

The observed radiance factor, $\beta_{obs}$, is related to the radiance factor inside the film just below the surface, $\beta^*$, by the relation $$\beta_{obs} = \{1 - r(\mu_o)\}\{[1 - r(\mu)]/n^2\}\beta^*$$

This in turn is related to the radiance factor calculated by radiative transfer theory in the absence of the refractive index change between the coating film and air, $\beta(\mu,\phi;\mu_o,\phi_o)$, by the equation $$\beta^*(\mu,\phi;\mu_o,\phi_o) = \beta(\mu,\phi;\mu_o,\phi_o) +$$

$$\frac{1}{\pi} \int_0^{2\pi} \int_0^1 \beta^*(\mu',\phi';\mu_o,\phi_o) r(\mu',\phi') \beta(\mu,\phi;\mu',\phi') \mu' d\mu' d\phi'$$

Continuing the single scattering assumption and introducing
$$r(\mu,\phi) = r(\mu)[\delta(\mu-\mu_o)/2\mu] 2\pi \delta(\phi-\phi_o)$$
for the specular boundary reflection, we obtain the following relation between $\beta^*$ and $\beta$
$$\beta^*(\mu,\phi;\mu_o,\phi_o) = \beta(\mu,\phi;\mu_o,\phi_o) / \{1 - r(\mu)\beta(\mu,\phi;\mu,\phi)\}$$
The observed or experimental radiance factor, $\beta_{obs}$, is $$\beta_{obs} = \frac{\{1 - r(\mu_o)\}\{[1 - r(\mu)]/n^2\}\beta(\mu,\phi;\mu_o,\phi_o)}{\{1 - r(\mu)\beta(\mu,\phi;\mu,\phi)\}}$$

Since $r(\mu)$ and $r(\mu_o)$ are in the range 0.04 to 0.06 for typical angles of incidence and view the corrected reflectance and measured reflectance are close enough to ignore these corrections as a first approximation for metallic color matching.

This finding is in contrast to that for solid colors where the diffuse scattering predominates leading to much larger corrections because of the total internal reflection of the diffuse light incident on the film air interface at angles greater than the critical angle.

COLOR MATCHING

Matching is the same whether for formulation or batch control. The measured parameters are compared with combinations of likely pigments to yield combinations that best approximate the desired color coating under various conditions.

Wavelength matching attempts to match the spectrophotometric reflectance curve as closely as possible simultaneously at each illuminating and viewing geometry of interest. This procedure works best when the pigments chosen for the match are the same as those present in the sample composition.

The following scheme can be used to estimate the least squares wavelength match to the reflectance curve. Weighting factors, W, may be used to emphasize the data at one or more geometries. At each geometry, l, for each wavelength, j, we have $$\beta_{lj} = \frac{\sigma_l * \mu_l * \mu_{ol} * \beta_{lj}^*}{(\mu_l + \mu_{ol}) * (K_{lj} + S_{lj}) + \sigma_{lj} * \mu_l * \mu_{ol}} + \beta s_{lj}$$

We can rewrite this equation as
$$\delta_l = \{(\beta_{lj} - \beta_{lj}^*) * (\mu_l + \mu_{ol}) * (K_{lj} + S_{lj})\} + \{(\beta_{lj} - \beta^*_{lj} - \beta s_{lj}) * \sigma_l * \mu_l * \mu_{ol}\} = 0$$

Define Q as $$Q = \sum_l W_l \sum_j \delta_{lj}^2$$

It is now required that the partial derivative of Q with respect to $c_m$, the concentration of the mth pigment, be zero for each nonmetallic and aluminum flake pigment. Thus $$\frac{\partial Q}{\partial c_m} = \sum_l W_l \sum_j \delta_{lj} \frac{\partial \delta}{\partial c_m} = 0$$

$$1 \leq m \leq N$$

where N is the total number of pigments in the sample. Introducing $$K_{lj} = \sum_i k_{lij} * c_i$$

$$S_{lj} = \sum_i s_{lij} * c_i$$

$$\sigma_{lj} = \sum_i \sigma_{lij} * c_i$$

Yielding $$\sum_i a_{im} * c_i = 0$$

$$1 \leq m \leq N$$

where

-continued $$a_{im} = \sum_l W_l \sum_j a_{lij} * a_{lmj}$$

and $$a_{lij} = \mu_l * \mu_{olj} * K_{lj} *(S - \beta_{lj})$$
for metal pigments $$a_{lij} = (S_{lj}/2) - \{\beta_{lj} *(\mu_{ol} + \mu_l) * (K_{lj} + S_{lj})\}$$
for colored pigments since concentrations are expressed in weight percent, the additional relationship is given $$\sum_i c_i = 100$$

Eliminating the Nth pigment, the set of equations which determine N−1 pigment concentrations $$100 * a_{Nm} = \sum_i (a_{Nm} - a_{im}) * c_i$$

$$1 \leq m \leq (N - 1)$$

The remaining or Nth pigment concentration is obtained by difference of the others from 100.

A wavelength match may be refined by using the resultant pigment concentrations as the starting point for a tristimulus match. This may lead to a more perceptually accurate match particularly when the pigments used to match the standard are different than those that were used to make the standard. Tristimulus matching is more sensitive to variations in panel preparation and measurement.

Various known tristimulus matching techniques can be used. A new method using a least squares tristimulus iteration procedure is particularly effective when matching metallic finishes simultaneously at multiple illuminating and viewing geometries. The three tristimulus values (X,Y,Z) at each geometry, l, are expanded in a Taylor series about a set of trial values of colorant concentrations, $c_i^0$. These equations are then solved for a set of $\Delta c_i$ values. The calculation is repeated with a new set of concentrations $c_i = c_i^0 + \Delta c_i$ until no improvement in the color match is obtained. To improve the method, the natural logarithm of the tristimulus value is expanded in a Taylor series as follows:

$$\log X_l = \log X_{ol} + \sum_i \left[\frac{\partial \log X_l}{\partial c_i}\right]_o * \Delta c_i$$

$$\log X_l = \log X_{ol} + \frac{1}{X_{ol}} \times \sum_i \left[\frac{\partial X_l}{\partial c_i}\right]_o * \Delta c_i$$

where the summation is taken over the N colorants in the coating. Thus the $\Delta c_i$ satisfy the following equations $$(\log X_{lk} - \log X_{lko}) * X_{lko} = \sum_i \left(\left[\frac{\partial X_{lk}}{\partial c_i}\right]_o - \left[\frac{\partial X_{lk}}{\partial c_N}\right]_o\right) * \Delta c_i$$

$$(\log Y_{lk} - \log Y_{lko}) * Y_{lko} = \sum_i \left(\left[\frac{\partial Y_{lk}}{\partial c_i}\right]_o - \left[\frac{\partial Y_{lk}}{\partial c_N}\right]_o\right) * \Delta c_i$$

$$(\log Z_{lk} - \log Z_{lko}) * Z_{lko} = \sum_i \left(\left[\frac{\partial Z_{lk}}{\partial c_i}\right]_o - \left[\frac{\partial Z_{lk}}{\partial c_N}\right]_o\right) * \Delta c_i$$

where the tristimulus values are now subscripted with k to denote the kth illuminant choice. In general the values of X, Y, Z are calculated for three illuminants to detect the degree of metamerism between the standard and match. As with wavelength matching, weighting factors, W, can be introduced to emphasize one or more geometries.

Now let $$\delta_{lxk} = (\log X_{lk} - \log X_{lko}) * X_{lko} =$$

$$\sum_i \left(\left[\frac{\partial X_{lk}}{\partial c_i}\right]_o - \left[\frac{\partial X_{lk}}{\partial c_N}\right]_o\right) * \Delta c_i$$

$$\delta_{lyk} = (\log Y_{lk} - \log Y_{lko}) * Y_{lko} =$$

$$\sum_i \left(\left[\frac{\partial Y_{lk}}{\partial c_i}\right]_o - \left[\frac{\partial Y_{lk}}{\partial c_N}\right]_o\right) * \Delta c_i$$

$$\delta_{lzk} = (\log Z_{lk} - \log Z_{lko}) * Z_{lko} =$$

$$\sum_i \left(\left[\frac{\partial Z_{lk}}{\partial c_i}\right]_o - \left[\frac{\partial Z_{lk}}{\partial c_N}\right]_o\right) * \Delta c_i$$

and define $$Q = \sum_l W_l \sum_k (\delta_{lxk}^2 + \delta_{lyk}^2 + \delta_{lzk}^2) \quad 1 \leq k \leq K$$

where the summation is made over the K illuminants chosen for matching. The method requires that the $\Delta c_i$ be determined to satisfy the following conditions $$\frac{\partial Q}{\partial \Delta c_m} = 0 \quad 1 \leq m \leq N - 1$$

This leads to the following equations for the $\Delta c_i$ $$\sum_k \beta_{lk} * a_{lkm} = \sum_i \Delta c_i * \sum_l W_l \sum_k a_{lki} a_{lkm} \quad 1 \leq m \leq N$$

where $$\beta_{lk} = (\log X_{lk} - \log X_{lko}) * X_{lko}$$

$$a_{lki} = \left[\frac{\partial X_{lk}}{\partial c_i}\right]_o - \left[\frac{\partial X_{lk}}{\partial c_N}\right]_o$$

$$\beta_{lk-1} = (\log Y_{lk} - \log Y_{lko}) * Y_{lko}$$

$$a_{l(k-1)i} = \left[\frac{\partial Y_{lk}}{\partial c_i}\right]_o - \left[\frac{\partial Y_{lk}}{\partial c_N}\right]_o$$

$$\beta_{lk-2} = (\log Z_{lk} - \log Z_{lko}) * Z_{lko}$$

$$a_{l(k-1)i} = \left[\frac{\partial Z_{lk}}{\partial c_i}\right]_o - \left[\frac{\partial Z_{lk}}{\partial c_N}\right]_o$$

and k now runs from 1 to 3K.

These equations are solved for the first $(N-1)$ $\Delta c_i$ values. Those values are then used to determine a new set of trial $c_i$ values and the process is continued by iteration until no further improvement in color difference between the standard and match is obtained.

This method appears to be superior to the conventional Allen procedure for reproducing the composition of metallic color panels. While the residual color differences at match may tend to be larger than those obtained by the Allen procedure, the match seems to be less metameric.

COLORANT CALIBRATION

Before color matches can be made or batches corrected, the absorption and scattering coefficients for the colored pigments must be determined. The cross section of the metal pigments must also be determined. The process of determining these constants is called pigment calibration. Whereas in color matching, the optical constants of the pigments are known and the concentrations required to match a standard color are determined, in pigment calibration, mixtures of known concentrations are used to determine the optical constants.

The optical constants are considered properties of the pigments as they are dispersed in a given resin system. Optical constants are wavelength dependent and must be calculated at each wavelength of interest. There are several techniques which may be used in determining the optical constants. In a typical pigment calibration a specific set of calibration panels is prepared at complete hiding, i.e., infinite optical thickness, and measured with a reflectance spectrophotometer at several illuminating and viewing geometries and at a number of wavelengths. The examples presented in this patent were done with a Datacolor MMK111 goniospectrophotometer which illuminates the sample at $-45$ degrees from the normal (to the left of the sample normal) and measures at 20, 0 and $-25$ degrees from the normal. Many researchers prefer describing the illuminating and viewing geometry in terms of the observation angle from the specular (mirror or gloss) angle. This convention will be followed in this patent. For the Datacolor MMK 111, the specular angle would be 45 degrees from the normal and the three geometries would be respectively described as 25 degrees from the specular angle, 45 degrees from the specular, and 70 degrees from the specular. Although the instrument measures a sample at 1 nm wavelength increments, the data was mathematically reduced to 20 nm increments from 400 to 700 nm, i.e., 400, 420, ..., 680, 700 nm. Another instrument that has been used successfully is the Macbeth 5010 goniospectrophotometer at 20, 45, and 75 degrees from the specular angle. The equations are not limited to those instruments, geometries, or wavelength ranges.

I. CALCULATING THE ALBEDO

In calibrating colorants it is sometimes necessary to know the albedo, $\omega$, that produced an observed reflectance in a panel containing no metal flake pigment. The albedo can be calculated by using the solid color radiative transfer theory and an iterative technique.

After correction for first surface affects (if desired), the internal radiance factor of a solid color can be found from $$\beta = \frac{\omega}{4} * \left[ \frac{H(\mu_o) * H(\mu)}{(\mu_o + \mu)} \right]$$

The value of $\omega$ is determined by using the secant method to find the root of the equation $$f(\omega) = \beta - \left\{ \frac{\omega}{4} * \left[ \frac{H(\mu_o) * H(\mu)}{(\mu_o + \mu)} \right] \right\}$$

The H function at a given angle, $\mu$, can be estimated by $$H(\mu) = \frac{1 + 2\mu}{1 + \lambda\mu}$$

where $$\lambda = 2 * (1-\omega)^{\frac{1}{2}}$$

or calculated with a computer by the methods previously described.

II. CALIBRATIONS USING A REFERENCE ALUMINUM PIGMENT

One technique of pigment calibration that has been used with success is to calibrate a reference aluminum (or other metal flake pigment), calibrate a black using a masstone of the black and a mixture of the black with aluminum, and to calibrate all other colorants using a mixture of the colorant in aluminum and either the colorant in black or a masstone of the colorant. In this technique the reflection coefficient for the reference aluminum flake, $r_{al}$, is equal to the reflectance of the masstone panel which may be corrected for the first surface affects, and the cross section for that reference flake, $\sigma_{al}$, is set equal 1.0.

Computations of the absorption and scattering coefficient are made using the downhill simplex method developed by Nelder and Mead and described by W. H. Press, B. P. Flannery, S. A. Teukolsky, and W. T. Vetterling in "Numerical Recipes" (Cambridge University Press, Cambridge, N.Y., and Melbourne, 1986). To use this technique, an initial estimate must be made for the absorption and scattering coefficients. The Nelder-Mead algorithm will adjust either just the absorption coefficient or both the absorption and scattering coefficients for each wavelength at each geometry until the sum of the squares of the difference between the experimental reflectance and the calculated reflectance is minimized. The minimized constants are then stored for later use in color matching and batch correction.

A. CALIBRATING A BLACK COLORANT OR OTHER OPAQUE COLORANT USING A MASSTONE AND A MIXTURE OF THE COLORANT IN THE REFERENCE ALUMINUM

Two panels are required to calibrate a black or other opaque colorant, a masstone of the colorant and a mixture of the colorant with the reference aluminum (or other metallic flake pigment). The reflection coefficient of the aluminum, $r_{al}$, the cross section of the aluminum, $\sigma_{al}$, the concentration of the reference aluminum, $c_{al}$, and the concentration of the black or other opaque colorant, $c_b$, in the colorant/aluminum mixture are known, and the reflectance of the colorant/aluminum mixture, $r_{mix}$, is measured and may be corrected for first surface affects.

Estimates of (K+S) and S are made at each wavelength for each geometry using the equations $$(K + S) = \frac{\mu_0 * \mu * (r_{al} - r_{mix}) * (\sigma_{al} * c_{al}/c_b)}{(\mu_0 + \mu) * r_{mix}}$$

$$S = (K + S) * \omega_b$$

in which $\omega_b$ is the albedo of the masstone. If (K+S) is less than S, a new estimate of (K+S) is made using $$(K+S) = S/\omega_b$$

An estimate of the absorption coefficient is then found by subtraction $$K = (K+S) - S$$

The estimates of K and S are processed with the Nelder-Mead algorithm and an optimized value for the absorption coefficient of the black or opaque colorant, $K_b$, is returned.

The scattering coefficient for the colorant, $S_b$, is then calculated from $$S_b = \frac{K * \omega_b}{(1 - \omega_b)}$$

B. CALIBRATING COLORANTS USING MIXTURES IN A REFERENCE ALUMINUM AND IN A CALIBRATED BLACK

Two panels are required to calibrate colorants using this technique, a mixture of the colorant with the reference aluminum (or other metallic flake pigment) and a mixture of the colorant with a calibrated black. The reflection coefficient of the aluminum, $r_{al}$, the cross section of the aluminum, $\sigma_{al}$, the concentration of the reference aluminum in the colorant/aluminum mixture, $c_{al}$, the concentration of colorant in the colorant/aluminum mixture, $c_{ca}$, the concentration of the calibrated black in the colorant/black mixture, $c_b$, the concentration of the colorant in the colorant/black mixture, $c_{cb}$, the absorption coefficient of the black, $K_b$, and the scattering coefficient of the black, $S_b$, are known. The reflectances of the colorant/aluminum mixture, $r_{ca}$, and the colorant/black mixture, $r_{cb}$, are measured and may be corrected for first surface affects.

Estimates of (K+S) and S for the colorant are then made at each wavelength for each geometry using the equations $$(K + S) = \frac{\mu_0 * \mu * (r_{al} - r_{ca}) * \sigma * c_{al}/c_{ca}}{(\mu_0 + \mu) * r_{ca}}$$

$$S = \{(K + S) * \omega_{cb}\} - \{c_b/c_{cb} * [S_b - (K_b + S_b) * \omega_{cb}]\}$$

If (K+S) is greater than or equal to S, then the estimate of the absorption coefficient is calculated from $$K = (K+S) - S$$

If (K+S) is less than S, then the estimate of the absorption coefficient is calculated from $$K = S - (K+S)$$

The estimates of K and S are processed with the Nelder-Mead algorithm and an optimized value of absorption coefficient for the colorant, $K_c$, is returned. The scattering coefficient for the colorant, $S_c$, is then calculated from $$S_c = \frac{(K_c * \omega_{cb}) - \{c_b/c_{cb} * [S_b - (K_b + S_b) * \omega_{cb}]\}}{(1 - \omega_{cb})}$$

C. CALIBRATING OTHER ALUMINUM PIGMENTS

Two panels are required to calibrate other aluminum pigments, a masstone of the other aluminum and a mixture of the other aluminum with a calibrated black. The concentration of the other aluminum in the black/aluminum mixture, $c_b$, and the concentration of the calibrated black in the black/aluminum mixture, $c_{al}$, the absorption coefficient of the calibrated black, $K_b$, and the scattering coefficient of the calibrated black, $S_b$, are known. The reflectance of the masstone aluminum and the calibrated black with aluminum mixture, $r_{ba}$, are measured and may be corrected for first surface affects.

The reflection coefficient for the other aluminum, $r_{al}$, is equal to the reflectance of the masstone panel which may be corrected for the first surface affects.

For other aluminum pigments, the Nelder-Mead algorithm is used to optimize the aluminum cross section in the black/aluminum mixture. The initial estimate of the cross section is $$\sigma = \frac{(\mu_0 - \mu) * (K_b + S_b)}{(\mu_0 + \mu) * (r_{al} - r_{ba})}$$

After optimizing, the other aluminum's cross section is calculated from $$\sigma_{al} = \sigma * c_{al}/c_b$$

III. CALIBRATIONS USING A REFERENCE WHITE PIGMENT

A second technique of colorant calibration uses calibration panels consisting of a reference white masstone, a mixture of the white with a black colorant, a masstone aluminum panel, a mixture of aluminum with the calibrated black colorant, and, for each additional colorant, a mixture of the colorant with the calibrated white and a mixture of the colorant with the calibrated black. Except for the aluminum panel, these equations presented with this technique can also be used to match solid colors using approximations to the full radiative transfer equation other than the Kubelka-Munk approximations. In the following descriptions it is understood that a different set of optical constants are being calculated for at each geometry for each wavelength measured. For this technique an iterative solution is shown. It is possible to use the Nelder-Mead algorithm to solve these equations.

A. CALIBRATING THE REFERENCE WHITE

To calibrate a reference white, a masstone panel containing the reference white colorant is required. For each geometry at each wavelength the scattering coefficient, S, is set equal to 1.0. For each reflectance value which may be corrected for the first surface reflections, the albedo, $\omega$, is computed. The absorption coefficient at each wavelength, K, is then $$K = (1.0/\omega) - 1.0$$

B. CALIBRATING BLACK AND OTHER OPAQUE COLORANTS

Two panels are required to calibrate a black colorant, a mixture of the black with the reference white and a black masstone. The concentration of the black, $c_b$, and the concentration of the reference white, $c_w$, in the black and white mixture are known as are the absorption, $K_w$, and scattering, $S_w$, coefficients for the reference white. For each reflectance value which may be corrected for the first surface corrections, the albedo for the black and white mixture, $\omega_{bw}$, and the albedo for the black masstone, $\omega_b$, are computed. From these quantities, the sum of the absorption and scattering coefficients, $(K+S)_{bw}$, for the black and white mixture can be calculated from $$(K + S)_{bw} = \left(\frac{c_w}{c_b}\right) * \left(\frac{S_w - \{(K_w + S_w) * \omega_{bw}\}}{\omega_{bw} - \omega_b}\right)$$

The scattering coefficient of the black is calculated from $$S_b = (K+S)_{bw} * \omega_b$$

and the absorption coefficient of the black is calculated from $$K_b = (K+S)_{bw} - S_b$$

Other colorants can be calibrated using these equations by preparing a mixture of the colorant in white and a masstone of the colorant and by calculating the appropriate concentrations and albedos. This technique should only be used when the masstone panel of the colorant can be prepared at complete hiding.

C. CALIBRATING OTHER NON-METALLIC COLORANTS

Two panels are required to calibrate other non-metallic colorants, a mixture of the colorant with the reference white and a mixture of the colorant with a calibrated black. The concentration of the colorant, $c_{cw}$, and the concentration of the reference white, $c_w$, in the colorant and white mixture are known as are the absorption, $K_w$, and scattering, $S_w$, coefficients of the reference white. The concentration of the colorant, $c_{cb}$, and the concentration of the calibrated black, $c_b$, in the colorant and black mixture are also known as are the absorption, $K_b$, and scattering, $S_b$, coefficients of the calibrated black. For each reflectance value which may be corrected for the first surface corrections, the albedo for the colorant and white mixture, $\omega_{cw}$, and the albedo for the colorant and black mixture, $\omega_{cb}$, are computed. From these quantities the scattering coefficient, $S_c$, of the colorant can be calculated as follows.

$$Y1 = \left(\frac{c_b}{c_c}\right) * [S_b - \{\omega_{cb} * (K_b + S_b)\}]$$

$$Y2 = \left(\frac{c_w}{c_c}\right) * [S_w - \{\omega_{cw} * (K_w + S_w)\}]$$

$$S_c = \frac{(\omega_{cb} * Y2) - (\omega_{cw} * Y1)}{(\omega_{cw} - \omega_{cb})}$$

The sum of the absorption and scattering coefficients for the colorant can also be calculated from these quantities and thus the absorption coefficient of the colorant itself as follows.

$$(K + S)_c = \frac{(Y1 + Y2)}{(\omega_{cw} - \omega_{cb})}$$

$$K_c = (K + S)_c - S_c$$

D. CALIBRATING METAL (ALUMINUM) PIGMENTS

With this technique two panels are required to calibrate a metal pigment, a masstone of the metal pigment and a mixture of the metal pigment and a calibrated black. The metal flake is usually aluminum but the equations are not restrictive to other metallic flake pigments. Aluminum will be assumed for the remainder of this discussion. The reflection coefficient of the aluminum flake, $r_{al}$, is equal to the reflectance of the masstone panel which may be corrected for the first surface affects. The cross section is found with an iterative procedure using the reflection coefficient and the radiance factors of the black and aluminum mixture, $\beta_{bm}$, which may be corrected for the first surface affects. The concentration of the aluminum flake, $c_{al}$, and the concentration of the calibrated black, $c_b$, are known as are the absorption, $K_b$, and scattering, $S_b$, coefficients of the calibrated black.

First an approximation of the aluminum cross section, $\sigma_{al}$, is made from the following equations.

$$R0 = \beta_{bm} - \frac{\{S_b/(K_b + S_b)\}}{\{4.0 * (\mu_o + \mu)\}}$$

$$\sigma_{al} = \frac{\{R0 * (\mu_o + \mu) * (K_b + S_b)\}}{\{\mu_o * \mu * (c_{al}/c_b) * (r_{al} - R0)\}}$$

The following iterative loop is performed until the difference between the variables R and R0 is sufficiently low, 0.00001 being a good ending point.

$$RA = \left(\frac{S_b}{2}\right) * \frac{1.0}{\{2 * (\mu_o + \mu) * (K_b + S_b)\} + \{\mu_o * \mu * (c_{al}/c_b)\}}$$

$$\frac{\sigma_{al} * (c_{al}/c_b)}{[\{2*(K_b + S_b)\} + \{\mu_o * \sigma_{al}*(c_{al}/c_b)\}] + [\{2*(K_b + S_b)\} + \{\mu*\sigma_{al}*(c_{al}/c_b)\}]}$$

$$R = r_{al} - RA$$

$$\sigma_{al} = \frac{\{R * (\mu_o + \mu) * (K_b + S_b)\}}{\{\mu_o * \mu * (c_{al}/c_b) * (r_{al} - R)\}}$$

$$R0 = R$$

E. CALIBRATING OTHER WHITE COLORANTS

Two panels are required to calibrate additional white colorants, a masstone of the white and a mixture of the white with a calibrated black. The concentration of the white, $c_w$, and the concentration of the calibrated black, $c_b$, in the white and black mixture are known as are the absorption, $K_b$, and scattering, $S_b$, coefficients for the calibrated white. For each radiance factor which may be corrected for the first surface affects, the albedo for the white masstone, $\omega_w$, and the albedo for the white and black mixture, $\omega_{wb}$, are computed. From these quantities, the sum of the absorption and scattering coefficients, $(K+S)_{wb}$, for the white and black mixture can be calculated from $$(K+S)_{wb} = \left(\frac{c_b}{c_w}\right) * \left(\frac{S_b - \{(K_b + S_b) * \omega_{wb}\}}{\omega_{wb} - \omega_w}\right)$$

The scattering coefficient of the new white is calculated from $$S_w = (K+S)_{wb} * \omega_w$$

and the absorption coefficient of the new white is calculated from $$K_w = (K+S)_{wb} * s_w$$

MATCHING

A strategy for matching solid colors is to make an initial match calculation using wavelength matching procedures followed by a least squares tristimulus refinement of the solution to the final match. The presently preferred matching method for metallic panels involves making a least squares wavelength match at all illuminating and viewing geometries of interest. The current state of the art techniques of panel preparation and measurement are neither as uniform nor as reproducible as with solid colors. Wavelength matching predicts panel compositions that are not as sensitive to experimental variations as is tristimulus matching. If the experimental variability can be lowered, the use of a tristimulus refinement might improve the final predictions.

For the examples following, three illuminating and viewing geometries are considered. This should not be considered as a limitation, however, since matches can be predicted for a single geometry. The maximum number of geometries is limited only by the measuring instruments commercially available and the size of the computer doing the calculations. All pigments used in the example were calibrated individually at each geometry. Following currently accepted practice, for the instrument used to generate the examples, each geometry is specified by the angle from the specular reflectance angle at which the specimen is viewed. The illumination was at 45 degrees to the specimen's normal, and viewing was at 25, 45, and 70 degrees from the specular reflectance angle. Other instrumental designs used to generate reflectances at multiple angles can be used equally as well.

EXAMPLES: TWO PIGMENT METALLIC MIXTURES

An example of a match of a mixture containing a single aluminum pigment and a single colored pigment is shown in the following table. The table lists the colorants, the parts of colorant in the sample, the calculated composition of the panel, and the color differences between the predicted match and the measured standard panel calculated for three selected illuminants.

| Colorant | Parts | Calc |
|---|---|---|
| Trans Red Oxide | 50 | 50.04 |
| Coarse Aluminum | 50 | 49.96 |
| DED 25 = 0.08 | DED 45 = 0.52 | DED 70 = 1.04 |

EXAMPLES: FOUR COLORANT METALLIC MIXTURES

A set of mixtures was prepared using four pigment blends made from one aluminum and three colored pigments. The match results are shown in the following tables. Pigments were calibrated individually, matches made at each geometry of interest (25, 45, and 70 degrees from the specular angle), and an overall least squares (LS) match made. Each table contains the panel identification, a listing of the pigments, the actual panel composition, the calculated panel compositions, and the color differences between the predicted matches and the measured standard panel calculated for daylight at each geometry of interest.

| Colorant | Parts | 25 Calc | 45 Calc | 70 Calc | LS Calc |
|---|---|---|---|---|---|
| Mixture 1A | | | | | |
| Phthalo Blue RS | 50 | 50.8 | 50.2 | 50.0 | 51.3 |
| Indo Yellow RS | 20 | 14.6 | 15.3 | 13.3 | 16.1 |
| Carbon Black S | 2 | 2.9 | 1.7 | 2.1 | 1.9 |
| Coarse Aluminum | 28 | 31.7 | 32.7 | 34.6 | 30.8 |
| Color Diff DED 25 | | 0.50 | — | — | 2.02 |
| Color Diff DED 45 | | — | 0.35 | — | 1.31 |
| Color Diff DED 70 | | — | — | 0.43 | 2.20 |
| Mixture 2A | | | | | |
| Phthalo Blue RS | 40 | 37.8 | 38.0 | 39.6 | 39.7 |
| Phthalo Green YS | 40 | 42.6 | 41.7 | 37.8 | 41.5 |
| Carbon Black S | 2 | 1.8 | 0.6 | 1.0 | 1.3 |
| Coarse Aluminum | 18 | 17.7 | 19.7 | 21.6 | 17.5 |
| Color Diff DED 25 | | 0.31 | — | — | 1.94 |
| Color Diff DED 45 | | — | 0.35 | — | 4.32 |
| Color Diff DED 70 | | — | — | 0.70 | 3.38 |
| Mixture 3A | | | | | |
| Phthalo Green YS | 50 | 57.0 | 52.5 | 51.5 | 54.2 |
| Indo Yellow GS | 20 | 14.7 | 18.0 | 18.6 | 19.0 |
| Carbon Black S | 2 | 2.7 | 1.3 | 0.9 | 1.8 |
| Coarse Aluminum | 28 | 25.7 | 28.2 | 29.0 | 25.0 |
| Color Diff DED 25 | | 0.08 | — | — | 3.56 |
| Color Diff DED 45 | | — | 0.27 | — | 3.01 |
| Color Diff DED 70 | | — | — | 0.25 | 4.84 |

The least square wavelength match provides a better overall prediction of the panel composition than the single geometry matches, but the predicted color difference is not as low. This is due to the variations in measurements and panel preparation.

The color matching and characterizations for coatings as described herein will usually be practiced in conjunction with computer software because of the lengthy mathematical calculations. Such computers can perform such calculations much faster than the traditional manual methods. Programs may be generated in many user languages which lend themselves to mathematical calculations; presently preferred software includes turbo pascal. Software lends itself to the practice of the invention especially in the color matching and batch correction processes where many reiterations may be required.

Figure 2:
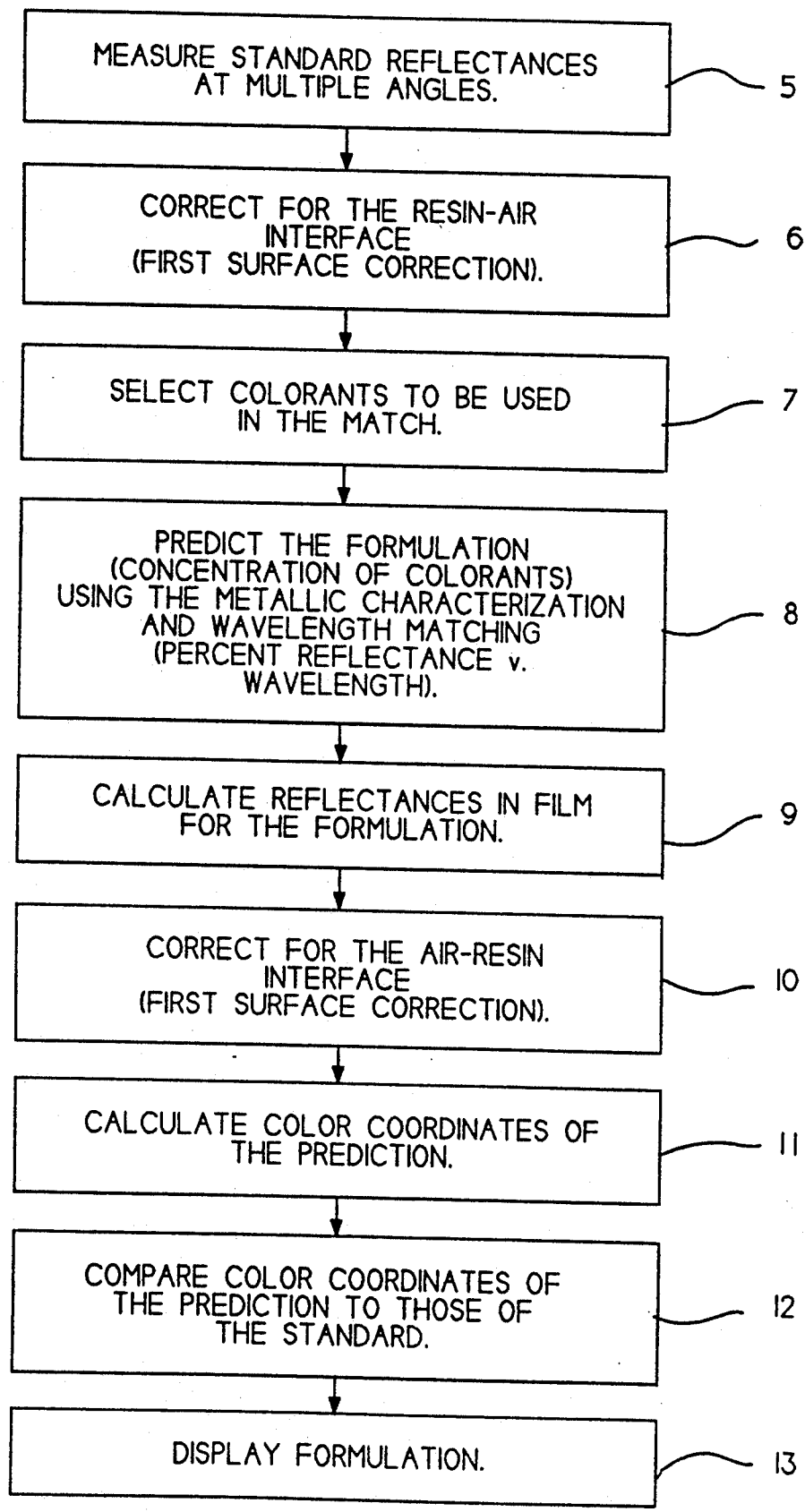
FIG. 2 is a flow chart showing some of the steps in a process using the invention for metallic color matching.

The flow chart shown in FIG. 2 is one presently preferred series of steps using multiple angle measurements for color matching a metallic coating, specifically a metallic paint coating. Referring to FIG. 2, the first step, 5, is a standard measurement of the reflectances at multiple angles. It is to be understood that while multiple angles are used in this embodiment, a single angle may also be used, with limitations, in the practice of this invention. Multiple angles may have specific advantages when it is desired to match the extreme "flop" that may be desirable in some coatings. The measured reflectances may then be corrected, step 6, for the resin/air interface as previously described herein. The next step, 7, includes selection of colorants to be used in the match. Past experience or manufacturing availability of the specific paint or pigments may strongly influence which colorants are used initially in the match. In step 8, the formulation defining the concentrations of the previously selected colorants is determined using a least squares wavelength matching method at each angle based upon the prior discussed characterizations of the light flux for both the measured sample and the selected colorants. In step 9, the reflectances of the formulation are then calculated using the prior discussed characterization method. In step 10, these reflectances may then be corrected for the air/resin interface similar to step 6. The color coordinates of the formulations are then calculated in step 11. The tristimulus values calculated in step 11 are then compared to the tristimulus values for the sample in step 12 and a color difference calculated. The desired match is displayed at step 14 or otherwise utilized.

Figure 3:
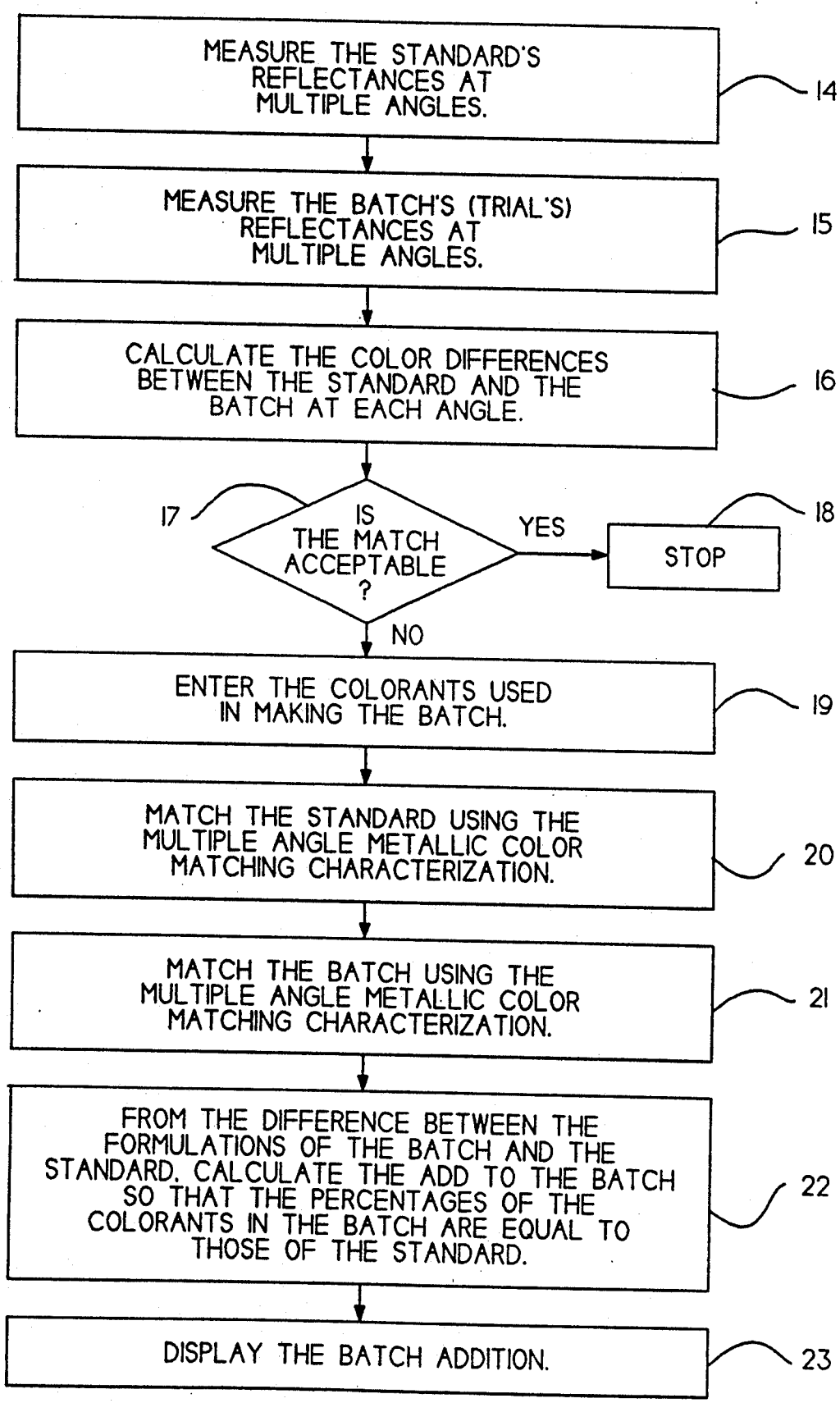
FIG. 3 is a flow chart showing some of the steps in a metallic batch correction process using the invention.

FIG. 3 shows a flow chart of a single angle metallic batch correction process using the teachings of the invention. The first step in such process, 14, is to measure the standard coatings reflectance at multiple angles. Single angle measurements could also be used within the scope of this invention with their inherent limitations. The measured reflectances are then recorded for the standard. Step 15 includes a similar measurement of the batch (trial) colors reflectances at multiple angles or at a single angle as step 14. The color differences between the standard and the batch are then calculated, 16. If the difference is acceptable in the decision, step 17, then the correction process can be stopped and the trial can be used as an acceptable duplication of the standard coating. If the color differences calculated in step 16 differ substantially from the standards, then the colorants used in the formulation of the trial enter the process, 19, and will be used to compare the characteristics with the standard to arrive at a batch addition. The multiple angle metallic color matching characterization process previously described herein is used then to characterize the standard, 20. The same metallic color matching process is as previously described and its related equations are used to describe the trial sample 21. The difference between the calculated formulations of the trial batch and the standard are then determined. The necessary additions of the colorants as actually used in the trial batch to match the standard are then calculated, 22. This calculation is done so that the percentages of the colorants in the revised batch are equal to those of those calculated for the standard as determined in step 20. The changes in concentrations and/or the additions of the colorants used in the trial are then displayed, 23, or otherwise used so that the batch can be corrected with such information. After the batch has been corrected it may be desirable to repeat the process steps 15 through 23 until an acceptable match in step 17 is achieved.

While certain presently preferred embodiments of the invention have been described hereinabove, it is to be understood that other methods of practicing the invention as will be apparent to those skilled in the art are included within the scope of the following claims.

We claim:

1. A method of characterization of a coating of a surface having metallic flakes distributed beneath a film within such coating, the method comprising the following steps:

(a) directing a beam or beams of light toward said coating;

(b) measuring the light leaving the coating from at least one predetermined angle from the outer surface of said coating;

(c) analyzing said measured light as a function of wavelength; and (d) characterizing said measured light as composed of the following components:

i. light from said beam reflected by said metal flake and attenuated on its exit route from the coating;

ii. light scattered in the entering path of the beam as it travels through the coating;

iii. light scattered by the reflected beam on its exit route from the coating;

iv. light scattered in the entering path then reflected by said metallic flake, and attenuated in the coating on the exiting path;

v. light scattered in the exiting path both to said metallic flake and reflected by said metallic flake and attenuated on its exit path from the coating.

2. The method of characterization of a coating of claim 1 further comprising:

said characterizing said measure light by the radiance factor ($\beta$) which is the sum of the direct radiance contribution of the incident beam reflected by the metal flake ($\beta_D$) and the scattered light contribution to the radiance ($\beta_S$) such that $$\beta = \beta_D + \beta_S.$$

3. A method of characterization of a coating of claim 2 further comprising:

said characterizing said measure light where the direct radiance contribution of the incident beam reflected by the metal flake is given by $$\beta(\mu,\phi;\mu_o,\phi_o) = \frac{\sigma\mu\mu_o \beta^*(\mu,\phi;\mu_o,\phi_o)}{(\mu + \mu_o)(K + S) + \sigma\mu\mu_o} + \beta_s$$

where $$\beta^*(\mu,\phi;\mu_o,\phi_o) = \frac{r(\mu,\phi;\mu_o,\phi_o)}{2\mu}$$

in which $\mu$ is the direction cosine of the angle of reflection at a given azimuthal angle;

$\phi$ is the azimuthal angle of the reflected radiation;

$\mu_o$ is the direction cosine of the angle of incident beam at a given azimuthal angle;

$\phi_o$ is the azimuthal angle of the incident beam;

$\sigma$ is the cross section of said metallic flake;

$r$ is the reflection coefficient of said metallic flake;

K is the absorption coefficient of said film;
S is the scattering coefficient of the film.

4. A method of characterization of a coating of claim 1 further comprising:
said characterizing said measure light by representing the metal flakes as mirrors reflecting light with no loss and attenuation where the contribution to the radiance of the scattered light is calculated as $$\beta_s = \frac{S}{2}\left[\frac{1}{2(\mu + \mu_o)(K + S) + \sigma\mu\mu_o} + \frac{\sigma}{\{2(K + S) + \sigma\mu_o\}\{2(K + S) + \sigma\mu\}}\right]$$

in which
$\mu$ is the direction cosine of the angle of reflection at a given azimuthal angle;
$\mu_o$ is the direction cosine of the angle of incident beam at a given azimuthal angle;
$\sigma$ is the cross section of said metallic flake;
K is the absorption coefficient of said film;
S is the scattering coefficient of the film.

5. The method of characterization of a coating of claim 1 further comprising:
said characterizing said measure light by representing the metal flakes as specular reflectors that have some loss or attenuation where the contribution of the scattered reflected light is calculated as $$\beta_s = \frac{\omega_o}{4(\mu + \mu_o)}\left[1 + \frac{\{r(\mu_o)\,r(\mu) - 1\}\sigma\mu\mu_o}{(\mu + \mu_o)(K + S) + \sigma\mu\mu_o} - \frac{r(\mu_o)\,r(\mu)\,\sigma\mu\mu_o}{2(\mu + \mu_o)(K + S) + \sigma\mu\mu_o}\right] +$$

$$\frac{\omega_o}{4(\mu - \mu_o)}\left[\frac{r(\mu)\,\sigma\mu}{2(K + S) + \sigma\mu} + \frac{\{R(\mu_o) - r(\mu)\}\sigma\mu\mu_o}{(\mu + \mu_o)(K + S) + \sigma\mu\mu_o} - \frac{r(\mu_o)\sigma\mu_o}{2(K + S) + \sigma\mu_o}\right]$$

in which
$\omega_o$ is the albedo of said metallic flake;
r is the reflectance of said metallic flake;
$\mu$ is the direction cosine of the angle of reflection at a given azimuthal angle;
$\mu_o$ is the direction cosine of the angle of incident beam at a given azimuthal angle;
$\sigma$ is the cross section of said metallic flake;
K is the absorption coefficient of said film;
S is the scattering coefficient of the film.

6. A method of characterization of a coating of a surface having metallic flakes distributed beneath a film within such coating, the method comprising the following steps:
(a) directing a beam of light toward said coating;
(b) measuring the light leaving the coating from at least one predetermined angle from the outer surface of said coating;
(c) analyzing said measured light as a function of wavelength; and
(d) calculating the light characteristics of said coating based upon the radiance factor ($\beta$) where $$\beta(\mu,\phi;\mu_o,\phi_o) = \frac{\sigma\mu\mu_o\beta^*(\mu,\phi;\mu_o,\phi_o)}{(\mu + \mu_o)(K + S) + \sigma\mu\mu_o} + \beta_s$$

where $$\beta^*(\mu,\phi;\mu_o,\phi_o) = \frac{r(\mu,\phi;\mu_o,\phi_o)}{2\mu}$$

in which
$\mu$ is the direction cosine of the angle of reflection at a given azimuthal angle;
$\phi$ is the azimuthal angle of the reflected radiation;
$\mu_o$ is the direction cosine of the angle of incident beam at a given azimuthal angle;
$\phi_o$ is the azimuthal angle of the incident beam;
$\sigma$ is the cross section of said metallic flakes;
r is the reflection coefficient of said metallic flake;
K is the absorption coefficient of said film;
S is the scattering coefficient of the film.

7. A method of characterization of a coating of a surface having metallic flakes distributed beneath a film within such coating, the method comprising the following steps:
(a) directing a beam of light toward said coating;
(b) measuring the light leaving the coating from at least one predetermined angle from the outer surface of said coating;
(c) analyzing said measured light as a function of wavelength; and
(d) calculating the light characteristics of said coating based upon the radiance factor ($\beta$) where $$\beta(\mu,\phi;\mu_o,\phi_o) = \frac{\sigma\mu\mu_o\beta^*(\mu,\phi;\mu_o,\phi_o)}{(\mu + \mu_o)(K + S) + \sigma\mu\mu_o} + \beta_s$$

where $$\beta^*(\mu,\phi;\mu_o,\phi_o) = \frac{r(\mu,\phi;\mu_o,\phi_o)}{2\mu}, \text{ and}$$

where $$\beta_s = \frac{S}{2}\left[\frac{1}{2(\mu + \mu_o)(K + S) + \sigma\mu\mu_o} + \frac{\sigma}{\{2(K + S) + \sigma\mu_o\}\{2(K + S) + \sigma\mu\}}\right]$$

in which
$\mu$ is the direction cosine of the angle of reflection at a given azimuthal angle;
$\phi$ is the azimuthal angle of the reflected radiation;
$\mu_o$ is the direction cosine of the angle of incident beam at a given azimuthal angle;
$\phi_o$ is the azimuthal angle of the incident beam;
$\sigma$ is the cross section of said metallic flake;
r is the reflection coefficient of said metallic flake;
K is the absorption coefficient of said film;
S is the scattering coefficient of the film.

8. A method of characterization of a coating of a surface having metallic flakes distributed beneath a film within such coating, the method comprising the following steps:
(a) directing a beam of light toward said coating;

(b) measuring the light leaving the coating from at least one predetermined angle from the outer surface of said coating;
(c) analyzing said measured light as a function of wavelength; and
(d) calculating the light characteristics of said coating based upon the radiance factor ($\beta$) where $$\beta(\mu,\phi;\mu_o,\phi_o) = \frac{\sigma\mu\mu_o\beta^*(\mu,\phi;\mu_o,\phi_o)}{(\mu + \mu_o)(K + S) + \sigma\mu\mu_o} + \beta_s$$

where $$\beta^*(\mu,\phi;\mu_o,\phi_o) = \frac{r(\mu,\phi;\mu_o,\phi_o)}{2\mu}, \text{ and}$$

where $$\beta_s = \frac{\omega_o}{4(\mu + \mu_o)}\left[1 + \frac{\{r(\mu_o)r(\mu) - 1\}\sigma\mu\mu_o}{(\mu + \mu_o)(K + S) + \sigma\mu\mu_o} - \frac{r(\mu_o)r(\mu)\sigma\mu\mu_o}{2(\mu + \mu_o)(K + S) + \sigma\mu\mu_o}\right] +$$

$$\frac{\omega_o}{4(\mu - \mu_o)}\left[\frac{r(\mu)\sigma\mu}{2(K + S) + \sigma\mu} + \frac{\{r(\mu_o) - r(\mu)\}\sigma\mu\mu_o}{(\mu + \mu_o)(K + S) + \sigma\mu\mu_o} - \frac{r(\mu_o)\sigma\mu_o}{2(K + S) + \sigma\mu_o}\right]$$

in which
$\omega_o$ is the albedo of said metallic flake;
$\mu$ is the direction cosine of the angle of reflection at a given azimuthal angle;
$\phi$ is the azimuthal angle of the reflected radiation;
$\mu_o$ is the direction cosine of the angle of incident beam at a given azimuthal angle;
$\phi_o$ is the azimuthal angle of the incident beam;
$\sigma$ is the cross section of said metallic flake;
r is the reflection coefficient of said metallic flake;
K is the absorption coefficient of said film;
S is the scattering coefficient of the film.

9. A method of color matching a coating having metallic flakes distributed in a film on a sample comprising:
(a) directing a beam of light toward said coating;
(b) measuring the light leaving the coating from at least one predetermined angle from the outer surface of said coating;
(c) analyzing said measured light as a function of wavelength;
(d) calculating the light characteristics of said sample from said measured light based upon the radiance factor ($\beta$) above where $$\beta(\mu,\phi;\mu_o,\phi_o) = \frac{\sigma\mu\mu_o\beta^*(\mu,\phi;\mu_o,\phi_o)}{(\mu + \mu_o)(K + S) + \sigma\mu\mu_o} + \beta_s$$

where $$\beta^*(\mu,\phi;\mu_o,\phi_o) = \frac{r(\mu,\phi;\mu_o,\phi_o)}{2\mu}, \text{ and}$$

in which
$\mu$ is the direction cosine of the angle of reflection at a given azimuthal angle;
$\phi$ is the azimuthal angle of the reflected radiation;
$\mu_o$ is the direction cosine of the angle of incident beam at a given azimuthal angle;
$\phi_o$ is the azimuthal angle of the incident beam;
$\sigma$ is the cross section of said metallic flake;
r is the reflection coefficient of said metallic flake;
K is the absorption coefficient of said film;
S is the scattering coefficient of the film;
(e) formulating trial coatings having various concentrations of pigments; and
(f) comparing the light characteristics of said trial coatings to said characteristics of said sample.

10. A method of color matching a coating having metallic flakes distributed in a film on a sample comprising:
(a) directing a beam of light toward said coating;
(b) measuring the light leaving the coating from at least one predetermined angle from the outer surface of said coating;
(c) analyzing said measured light as a function of wavelength;
(d) calculating the light characteristics of said sample from said measured light based upon the radiance factor ($\beta$) above where $$\beta(\mu,\phi;\mu_o,\phi_o) = \frac{\sigma\mu\mu_o\beta^*(\mu,\phi;\mu_o,\phi_o)}{(\mu + \mu_o)(K + S) + \sigma\mu\mu_o} + \beta_s$$

where $$\beta^*(\mu,\phi;\mu_o,\phi_o) = \frac{r(\mu,\phi;\mu_o,\phi_o)}{2\mu}, \text{ and}$$

where $$\beta_s = \frac{S}{2}\left[\frac{1}{2(\mu + \mu_o)(K + S) + \sigma\mu\mu_o} + \frac{\sigma}{\{2(K + S) + \sigma\mu_o\}\{2(K + S) + \sigma\mu\}}\right]$$

in which
$\mu$ is the direction cosine of the angle of reflection at a given azimuthal angle;
$\phi$ is the azimuthal angle of the reflected radiation;
$\mu_o$ is the direction cosine of the angle of incident beam at a given azimuthal angle;
$\phi_o$ is the azimuthal angle of the incident beam;
$\sigma$ is the cross section of said metallic flake;
r is the reflection coefficient of said metallic flake;
K is the absorption coefficient of said film;
S is the scattering coefficient of the film;
(e) formulating trial coatings having various concentrations of pigments; and
(f) comparing the light characteristics of said trial coatings to said characteristics of said sample.

11. A method of color matching a coating having metallic flakes distributed in a film on a sample comprising:
(a) directing a beam of light toward said coating;
(b) measuring the light leaving the coating from at least one predetermined angle from the outer surface of said coating;
(c) analyzing said measured light as a function of wavelength;
(d) calculating the light characteristics of said sample from said measured light based upon radiance factor ($\beta$) above where $$\beta(\mu,\phi;\mu_o,\phi_o) = \frac{\sigma\mu\mu_o\beta^*(\mu,\phi;\mu_o,\phi_o)}{(\mu + \mu_o)(K + S) + \sigma\mu\mu_o} + \beta_s$$

where $$\beta^*(\mu,\phi;\mu_o,\phi_o) = \frac{r(\mu,\phi;\mu_o,\phi_o)}{2\mu}, \text{ and}$$

where $$\beta_s = \frac{\omega_o}{4(\mu + \mu_o)} \left[ 1 + \frac{\{r(\mu_o)r(\mu) - 1\}\sigma\mu\mu_o}{(\mu + \mu_o)(K + S) + \sigma\mu\mu_o} - \right.$$

$$\left. \frac{r(\mu_o)r(\mu)\sigma\mu\mu_o}{2(\mu + \mu_o)(K + S) + \sigma\mu\mu_o} \right] +$$

$$\frac{\omega_o}{4(\mu - \mu_o)} \left[ \frac{r(\mu)\sigma\mu}{2(K + S) + \sigma\mu} + \right.$$

$$\left. \frac{\{r(\mu_o) - r(\mu)\}\sigma\mu\mu_o}{(\mu + \mu_o)(K + S) + \sigma\mu\mu_o} - \frac{r(\mu_o)\sigma\mu_o}{2(K + S) + \sigma\mu_o} \right]$$

in which $\omega_o$ is the albedo of said metallic flake;

$\mu$ is the direction cosine of the angle of reflection at a given azimuthal angle;

$\phi$ is the azimuthal angle of the reflected radiation;

$\mu_o$ is the direction cosine of the angle of incident beam at a given azimuthal angle;

$\phi_o$ is the azimuthal angle of the incident beam;

$\sigma$ is the cross section of said metallic flake;

r is the reflection coefficient of said metallic flake;

K is the absorption coefficient of said film;

S is the scattering coefficient of the film;

(e) formulating trial coatings having various concentrations of pigments; and (f) comparing the light characteristics of said trial coatings to said characteristics of said sample.

12. The method of color matching of claim 9 wherein said comparing said light characterization of said trial coatings to the light characterization of said sample further comprises wavelength comparison within the spectral range of said measuring.

13. The method of color matching of claim 10 wherein said comparing said light characterization of said trial coatings to the light characterization of said sample further comprises wavelength comparison within the spectral range of said measuring.

14. The method of color matching of claim 11 wherein said comparing said light characterization of said trial coatings to the light characterization of said sample further comprises wavelength comparison within the spectral range of said measuring.

15. The method of color matching of claim 9 wherein said comparing said light characteristics of said trial coatings to the light characteristics of said sample further comprises comparison of the respective tristimulus values for said sample and said trial formulation.

16. The method of color matching of claim 10 wherein said comparing said light characteristics of said trial coatings to the light characteristics of said sample further comprises comparison of the respective tristimulus values for said sample and said trial formulation.

17. The method of color matching of claim 11 wherein said comparing said light characteristics of said trial coatings to the light characteristics of said sample further comprises comparison of the respective tristimulus values for said sample and said trial formulation.

18. The method of color matching of claim 13 wherein said comparison of the respective tristimulus values for said sample and said trial formulation comparison comprises minimizing the sum of the square of the deviation of tristimulus values between said sample and said trial formulation.

19. The method of color matching of claim 14 wherein said comparison of the respective tristimulus values for said sample and said trial formulation comparison comprises minimizing the sum of the square of the deviation of tristimulus values between said sample and said trial formulation.

20. The method of color matching of claim 15 wherein said comparison of the respective tristimulus values for said sample and said trial formulation comparison comprises minimizing the sum of the square of the deviation of tristimulus values between said sample and said trial formulation.

21. The method of color matching of claim 9 wherein said comparing said light characteristics of said trial coatings to said light characteristics of said sample further comprises the steps of first wavelength comparing within the spectral range of said measuring; and comparing of the respective tristimulus values for said sample and said trial formulation comparison comprises minimizing the sum of the square of the deviation of tristimulus values between said sample and said trial formulation.

22. The method of color matching of claim 10 wherein said comparing said light characteristics of said trial coatings to said light characteristics of said sample further comprises the steps of first wavelength comparing within the spectral range of said measuring; and comparing of the respective tristimulus values for said sample and said trial formulation comparison comprises minimizing the sum of the square of the deviation of tristimulus values between said sample and said trial formulation.

23. The method of color matching of claim 11 wherein said comparing said light characteristics of said trial coatings to said light characteristics of said sample further comprises the steps of first wavelength comparing within the spectral range of said measuring; and comparing of the respective tristimulus values for said sample and said trial formulation comparison comprises minimizing the sum of the square of the deviation of tristimulus values between said sample and said trial formulation.

* * * * *